(12) United States Patent
Pratt et al.

(10) Patent No.: US 12,204,009 B2
(45) Date of Patent: Jan. 21, 2025

(54) USING SCENT FINGERPRINTS AND SOUND FINGERPRINTS FOR LOCATION AND PROXIMITY DETERMINATIONS

(71) Applicant: AT&T Intellectual Property I, L.P., Atlanta, GA (US)

(72) Inventors: James Pratt, Round Rock, TX (US); Eric Zavesky, Austin, TX (US); Nigel Bradley, Canton, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 665 days.

(21) Appl. No.: 17/218,704

(22) Filed: Mar. 31, 2021

(65) Prior Publication Data

US 2022/0317272 A1   Oct. 6, 2022

(51) Int. Cl.
*G01S 11/14* (2006.01)
*G01N 27/00* (2006.01)
(Continued)

(52) U.S. Cl.
CPC .............. *G01S 11/14* (2013.01); *G01N 27/00* (2013.01); *G01N 33/0031* (2013.01);
(Continued)

(58) Field of Classification Search
CPC .............. G01S 11/14; G01S 5/18; G01S 5/16; G01S 3/8083; G01S 11/12; G01S 15/88;
(Continued)

(56) References Cited

U.S. PATENT DOCUMENTS

2005/0267596 A1*  12/2005  Chen ..................... A61F 5/0033
                                                    606/192
2019/0287311 A1*   9/2019  Bhatnagar ............... G06T 15/08
2021/0141049 A1*   5/2021  Nurminen ........... G01S 5/02525

FOREIGN PATENT DOCUMENTS

CN        104865555 A  *  8/2015    ............... G01S 5/22
CN        108810838 A  * 11/2018    ........... G01S 5/0252
(Continued)

OTHER PUBLICATIONS

Kwon et al. (Multiple Odor Recognition and Source Direction Estimation with an Electronic Nose System. International Journal of Distributed Sensor Networks. 2013;9(8). doi:10.1155/2013/361378) (Year: 2013).*
(Continued)

*Primary Examiner* — Daniel R Miller
*Assistant Examiner* — Christian T Bryant
(74) *Attorney, Agent, or Firm* — Hartman & Citrin LLC

(57) ABSTRACT

Using scent fingerprints and sound fingerprints for location and proximity determinations can include detecting a movement of a user device relative to an environment, and determining if a fingerprint associated with the user device and the environment is available. The fingerprint can include a sound fingerprint, a scent fingerprint, and usage data defining resource usage of the user device at the environment, The fingerprint associated with the user device and the environment can be obtained with an instance of sensor data including a scent detected at the user device and a sound detected at the user device. Based on the instance of sensor data and the fingerprint associated with the user device and the environment, a location and proximity of the user device can be determined.

20 Claims, 7 Drawing Sheets

(51) Int. Cl.
| | | |
|---|---|---|
| *G01N 33/497* | (2006.01) | |
| *G01S 5/16* | (2006.01) | |
| *G01S 5/18* | (2006.01) | |
| *G01S 11/06* | (2006.01) | |
| *G01S 11/12* | (2006.01) | |
| *G01S 15/88* | (2006.01) | |
| *G01N 33/00* | (2006.01) | |
| *G01S 3/808* | (2006.01) | |
| *G01S 5/02* | (2010.01) | |

(52) U.S. Cl.
CPC ....... *G01N 33/0047* (2013.01); *G01N 33/497* (2013.01); *G01S 3/8083* (2013.01); *G01S 5/0295* (2020.05); *G01S 5/16* (2013.01); *G01S 5/18* (2013.01); *G01S 11/06* (2013.01); *G01S 11/12* (2013.01); *G01S 15/88* (2013.01)

(58) Field of Classification Search
CPC ................... G01S 11/06; G01S 5/0295; G01N 33/0031; G01N 33/0047; G01N 33/497; G01N 27/00

See application file for complete search history.

(56) References Cited

FOREIGN PATENT DOCUMENTS

| | | | |
|---|---|---|---|
| CN | 108896962 A | * 11/2018 | ............... G01S 5/18 |
| CN | 111965600 A | * 11/2020 | |

OTHER PUBLICATIONS

Schuman, Evan, "The game-changing potential of smartphones that can smell," retrieved at https://www.computerworld.com/article/3278594/the-game-changing-potential-of-smartphones-that-can-smell.html on Mar. 9, 2021.

* cited by examiner

USING SCENT FINGERPRINTS AND SOUND FINGERPRINTS FOR LOCATION AND PROXIMITY DETERMINATIONS

BACKGROUND

For proximal services and applications, recognition and context understanding methods can be increasingly integrated into daily life applications (cameras, ubiquitous displays, beacon navigation, etc.). In the location services space, identification and authentication methods utilizing triangulation, for example, and traditional aerial service providers such as the global positioning system ("GPS") may fail to accurately differentiate indoor locations wherein GPS line of sight may be unavailable.

Furthermore, using GPS and/or other known technologies for determining location may not enable providers to draw similarities between similar contexts. For example, providers may not detect similarities between a library and a classroom, by way of example, without rich secondary point-of-interest databases.

SUMMARY

The present disclosure is directed to using scent fingerprints and sound fingerprints for location and proximity determinations. A user device can move relative to an environment. For example, the user device may move into an environment, through the environment, out of the environment, between two environments, and/or among other environments and/or other locations. The user device can generate, using one or more sensors, an instance of sensor data that can be provided to a server computer. The sensor data can include geographic location information, scent data, sound data, movement data, environment data (e.g., temperature information, etc.), and/or other data (e.g., data that represents resources accessible to the user device, applications executing at the user device, or the like). The server computer can be configured, e.g., via execution of a location and proximity service, to generate, based on the sensor data, a fingerprint that describes sounds and smells associated with one or more geographic locations and/or proximities of the user device (e.g., devices and/or entities in a proximity of the user device), as well as resources being used and/or accessed by the user device at particular locations and/or proximities. The fingerprint can be stored or immediately used for various purposes.

In particular, the server computer can be configured to detect a movement of the user device relative to an environment, and to determine if a user or other entity associated with the user device has opted in to, or opted out from, using scent and/or sound to determine location and/or proximity. In some embodiments, the user device can be queried for an opt-in/opt-out decision by the location and proximity service (e.g., at setup time and/or at any other time), while in some other embodiments the user device can define opt-in and/or opt-out preferences at the user device (e.g., during installation, activation, and/or configuration of the location and proximity application). Because the opt-in and/or opt-out decision can be obtained from the user device in additional and/or alternative manners, it should be understood that these examples are illustrative, and therefore should not be construed as being limiting in any way.

If the user device has opted-in to use scent and sound for determining location and/or proximity, the location and proximity service can be configured to determine if a fingerprint is stored for the user device and/or the associated location relative to which the movement was detected. If a fingerprint is not stored and/or accessible, the location and proximity service can be configured to create a fingerprint. If a fingerprint is stored and/or is accessible, the location and proximity service can obtain the fingerprint associated with the user device and the location, as well as an additional release of the sensor data.

The location and proximity service can compare the additional release of the sensor data to the fingerprint to determine where the user device is located. Namely, the sound and/or scent information from the sensor data can be compared to the sound fingerprint and/or scent fingerprint in the fingerprint to determine a relative location of the user device to the location and/or proximity captured by the fingerprint. It can be appreciated that multiple fingerprints can be used to determine where the user device is located, based on sound and/or scent information, among other data.

Upon determining a location and/or proximity of the user device, the location and proximity service can determine if an action should be taken. Namely, the fingerprints can also define; for specific locations, scent profiles or fingerprints, sound profiles or fingerprints, proximities, and the like; resources that were accessed and/or used by the user device. Thus, for example, the fingerprint can define, for a particular location and device, one or more applications being used at the user device; one or more resources being accessed by the user device; a sound fingerprint at the user device; a scent fingerprint at the user device; combinations thereof; or the like. Thus, the fingerprints can be used to determine location and proximity, and also to determine resources accessed and/or used by the user device at the various locations and/or proximities. It should be understood that this example is illustrative, and therefore should not be construed as being limiting in any way.

If the location and proximity service determines that an action should be taken (or triggered), the location and proximity service can generate one or more commands for taking or triggering the action. Thus, for example, the location and proximity service can generate a command that, when received by the computing device, causes the computing device to host a resource, make the resource available, activate a service, or otherwise make the resource available to the user device. The command also can include instructions that, when received by the user device, cause the user device to activate or access a resource such as the resource, an application installed at the user device, and/or other resources. The location and proximity service can update the fingerprint to reflect the most recent use, in some embodiments. It should be understood that this example is illustrative, and therefore should not be construed as being limiting in any way.

According to one aspect of the concepts and technologies disclosed herein, a system is disclosed. The system can include a processor and a memory. The memory can store computer-executable instructions that, when executed by the processor, cause the processor to perform operations. The operations can include detecting a movement of a user device relative to an environment; and determining if a fingerprint associated with the user device and the environment is available. The fingerprint can include a sound fingerprint, a scent fingerprint, and usage data defining resource usage of the user device at the environment. The operations further can include obtaining the fingerprint associated with the user device and the environment; obtaining an instance of sensor data including a scent detected at the user device, and a sound detected at the user device; and determining, based on the instance of sensor data and the fingerprint associated with the user device and the environment, a location and proximity of the user device.

In some embodiments, obtaining the fingerprint can include obtaining a further instance of sensor data; determining, based on the further instance of sensor data, a location of the user device in the environment, the scent fingerprint at the location of the user device in the environment, the sound fingerprint at the location of the user device in the environment, and resource usage of the user device at the location of the user device in the environment; and recording the fingerprint. The fingerprint can include an identifier of the user device, location data that identifies the location of the user device in the environment, the sound fingerprint at the location of the user device in the environment, the scent fingerprint at the location of the user device in the environment, and the resource usage of the user device at the location of the user device in the environment. Obtaining the fingerprint further can include storing the fingerprint.

In some embodiments, the sound fingerprint can include a first sound recorded at the location of the user device in the environment, a first level associated with the first sound, and a first frequency of the first sound; and a second sound recorded at the location of the user device in the environment, a second level associated with the second sound, and a second frequency of the second sound. In some embodiments, the scent fingerprint can include a first sound recorded at the location of the user device in the environment, a first level associated with the first sound, and a first frequency of the first sound; and a second sound recorded at the location of the user device in the environment, a second level associated with the second sound, and a second frequency of the second sound.

In some embodiments, the computer-executable instructions, when executed by the processor, can cause the processor to perform operations further including determining, based on the location and proximity of the user device, if an action should be taken; and in response to a determination that the action should be taken, triggering the action by generating a command and sending the command to a computing device. The computing device can be configured to make available to the user device a resource in response to receiving the command.

According to another aspect of the concepts and technologies disclosed herein, a method is disclosed. The method can include detecting, at a computer including a processor, a movement of a user device relative to an environment; and determining, by the processor, if a fingerprint associated with the user device and the environment is available. The fingerprint can include a sound fingerprint, a scent fingerprint, and usage data defining resource usage of the user device at the environment. The method further can include obtaining, by the processor, the fingerprint associated with the user device and the environment; obtaining, by the processor, an instance of sensor data including a scent detected at the user device, and a sound detected at the user device; and determining, by the processor and based on the instance of sensor data and the fingerprint associated with the user device and the environment, a location and proximity of the user device.

In some embodiments, the method further can include determining, based on the location and proximity of the user device, if an action should be taken; and in response to a determination that the action should be taken, triggering the action. In some embodiments, triggering the action can include generating a command and sending the command to a computing device. The computing device can be configured to make available to the user device a resource in response to receiving the command. In some embodiments, triggering the action can include generating a command that, when received by the user device, can cause the user device to activate an application at the user device.

In some embodiments, the method further can include determining, by the processor, if the user device has opted-in to use scent and sound to determine location and proximity. In some embodiments, obtaining the fingerprint associated with the user device and the environment can include creating the fingerprint. In some embodiments, obtaining the fingerprint associated with the user device and the environment can include retrieving the fingerprint.

In some embodiments, obtaining the fingerprint can include obtaining a further instance of sensor data; determining, based on the further instance of sensor data, a location of the user device in the environment, the scent fingerprint at the location of the user device in the environment, the sound fingerprint at the location of the user device in the environment, and resource usage of the user device at the location of the user device in the environment; and recording the fingerprint. The fingerprint can include an identifier of the user device, location data that identifies the location of the user device in the environment, the sound fingerprint at the location of the user device in the environment, the scent fingerprint at the location of the user device in the environment, and the resource usage of the user device at the location of the user device in the environment. Obtaining the fingerprint further can include storing the fingerprint In some embodiments, the sound fingerprint can include a first sound recorded at the location of the user device in the environment, a first level associated with the first sound, and a first frequency of the first sound; and a second sound recorded at the location of the user device in the environment, a second level associated with the second sound, and a second frequency of the second sound. In some embodiments, the scent fingerprint can include a first sound recorded at the location of the user device in the environment, a first level associated with the first sound, and a first frequency of the first sound; and a second sound recorded at the location of the user device in the environment, a second level associated with the second sound, and a second frequency of the second sound.

According to yet another aspect of the concepts and technologies disclosed herein, a computer storage medium is disclosed. The computer storage medium can store computer-executable instructions that, when executed by a processor, cause the processor to perform operations. The operations can include detecting a movement of a user device relative to an environment; and determining if a fingerprint associated with the user device and the environment is available. The fingerprint can include a sound fingerprint, a scent fingerprint, and usage data defining resource usage of the user device at the environment. The operations further can include obtaining the fingerprint associated with the user device and the environment; obtaining an instance of sensor data including a scent detected at the user device, and a sound detected at the user device; and determining, based on the instance of sensor data and the fingerprint associated with the user device and the environment, a location and proximity of the user device.

In some embodiments, obtaining the fingerprint can include obtaining a further instance of sensor data; determining, based on the further instance of sensor data, a location of the user device in the environment, the scent fingerprint at the location of the user device in the environment, the sound fingerprint at the location of the user device in the environment, and resource usage of the user device at the location of the user device in the environment; and recording the fingerprint. The fingerprint can include an identifier of the user device, location data that identifies the location of the user device in the environment, the sound fingerprint at the location of the user device in the environment, the scent fingerprint at the location of the user device in the environment, and the resource usage of the user device at the location of the user device in the environment. Obtaining the fingerprint further can include storing the fingerprint In some embodiments, the sound fingerprint can include a first sound recorded at the location of the user device in the environment, a first level associated with the first sound, and a first frequency of the first sound; and a second sound recorded at the location of the user device in the environment, a second level associated with the second sound, and a second frequency of the second sound. In some embodiments, the scent fingerprint can include a first sound recorded at the location of the user device in the environment, a first level associated with the first sound, and a first frequency of the first sound; and a second sound recorded at the location of the user device in the environment, a second level associated with the second sound, and a second frequency of the second sound.

In some embodiments, the computer-executable instructions, when executed by the processor, can cause the processor to perform operations further including determining, based on the location and proximity of the user device, if an action should be taken; and in response to a determination that the action should be taken, triggering the action by generating a command and sending the command to a computing device. The computing device can be configured to make available to the user device a resource in response to receiving the command.

Other systems, methods, and/or computer program products according to embodiments will be or become apparent to one with skill in the art upon review of the following drawings and detailed description. It is intended that all such additional systems, methods, and/or computer program products be included within this description and be within the scope of this disclosure.

DETAILED DESCRIPTION

Figure 1:
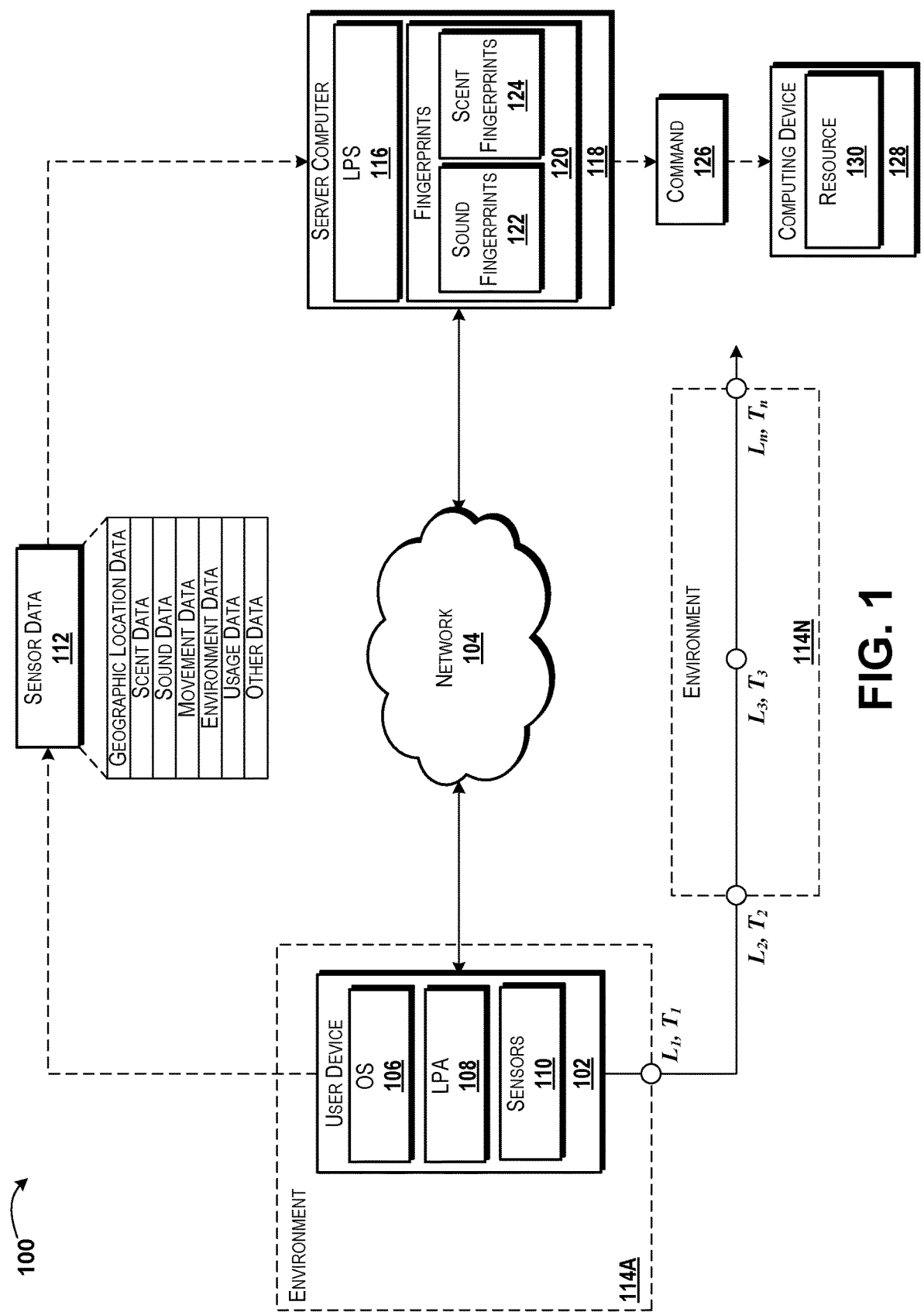
FIG. 1 is a system diagram illustrating an illustrative operating environment for various embodiments of the concepts and technologies described herein.

The following detailed description is directed to using scent fingerprints and sound fingerprints for location and proximity determinations. A user device can move relative to an environment. For example, the user device may move into an environment, through the environment, out of the environment, between two environments, and/or among other environments and/or other locations. The user device can generate, using one or more sensors, an instance of sensor data that can be provided to a server computer. The sensor data can include geographic location information, scent data, sound data, movement data, environment data (e.g., temperature information, etc.), and/or other data (e.g., data that represents resources accessible to the user device, applications executing at the user device, or the like). The server computer can be configured, e.g., via execution of a location and proximity service, to generate, based on the sensor data, a fingerprint that describes sounds and smells associated with one or more geographic locations and/or proximities of the user device (e.g., devices and/or entities in a proximity of the user device), as well as resources being used and/or accessed by the user device 102 at particular locations and/or proximities. The fingerprint can be stored or immediately used for various purposes.

In particular, the server computer can be configured to detect a movement of the user device relative to an environment, and to determine if a user or other entity associated with the user device has opted in to, or opted out from, using scent and/or sound to determine location and/or proximity. In some embodiments, the user device can be queried for an opt-in/opt-out decision by the location and proximity service (e.g., at setup time and/or at any other time), while in some other embodiments the user device can define opt-in and/or opt-out preferences at the user device (e.g., during installation, activation, and/or configuration of the location and proximity application). Because the opt-in and/or opt-out decision can be obtained from the user device in additional and/or alternative manners, it should be understood that these examples are illustrative, and therefore should not be construed as being limiting in any way.

If the user device has opted-in to use scent and sound for determining location and/or proximity, the location and proximity service can be configured to determine if a fingerprint is stored for the user device and/or the associated location relative to which the movement was detected. If a fingerprint is not stored and/or accessible, the location and proximity service can be configured to create a fingerprint. If a fingerprint is stored and/or is accessible, the location and proximity service can obtain the fingerprint associated with the user device and the location, as well as an additional release of the sensor data.

The location and proximity service can compare the additional release of the sensor data to the fingerprint to determine where the user device is located. Namely, the sound and/or scent information from the sensor data can be compared to the sound fingerprint and/or scent fingerprint in the fingerprint to determine a relative location of the user device to the location and/or proximity captured by the fingerprint. It can be appreciated that multiple fingerprints can be used to determine where the user device is located, based on sound and/or scent information, among other data.

Upon determining a location and/or proximity of the user device, the location and proximity service can determine if an action should be taken. Namely, the fingerprints can also define; for specific locations, scent profiles or fingerprints, sound profiles or fingerprints, proximities, and the like; resources that were accessed and/or used by the user device. Thus, for example, the fingerprint can define, for a particular location and device, one or more applications being used at the user device; one or more resources being accessed by the user device; a sound fingerprint at the user device; a scent fingerprint at the user device; combinations thereof; or the like. Thus, the fingerprints can be used to determine location and proximity, and also to determine resources accessed and/or used by the user device at the various locations and/or proximities. It should be understood that this example is illustrative, and therefore should not be construed as being limiting in any way.

If the location and proximity service determines that an action should be taken (or triggered), the location and proximity service can generate one or commands for taking or triggering the action. Thus, for example, the location and proximity service can generate a command that, when received by the computing device, causes the computing device to host a resource, make the resource available, activate a service, or otherwise make the resource available to the user device. The command also can include instructions that, when received by the user device, causes the user device to activate or access a resource such as the resource, an application installed at the user device, and/or other resources. The location and proximity service can update the fingerprint to reflect the most recent use, in some embodiments. It should be understood that this example is illustrative, and therefore should not be construed as being limiting in any way.

While the subject matter described herein is presented in the general context of program modules that execute in conjunction with the execution of an operating system and application programs on a computer system, those skilled in the art will recognize that other implementations may be performed in combination with other types of program modules. Generally, program modules include routines, programs, components, data structures, and other types of structures that perform particular tasks or implement particular abstract data types. Moreover, those skilled in the art will appreciate that the subject matter described herein may be practiced with other computer system configurations, including hand-held devices, multiprocessor systems, microprocessor-based or programmable consumer electronics, minicomputers, mainframe computers, and the like.

Referring now to FIG. 1, aspects of an operating environment 100 for various embodiments of the concepts and technologies disclosed herein for using scent fingerprints and sound fingerprints for location and proximity determinations will be described, according to an illustrative embodiment. The operating environment 100 shown in FIG. 1 includes a user device 102. The user device 102 can operate in communication with and/or as part of a communications network ("network") 104, though this is not necessarily the case.

According to various embodiments, the functionality of the user device 102 may be provided by one or more mobile telephones, smartphones, laptop computers, tablet computers, other computing systems, and the like. It should be understood that the functionality of the user device 102 can be provided by a single device, by two or more similar devices, and/or by two or more dissimilar devices. For purposes of describing the concepts and technologies disclosed herein, the user device 102 is described herein as a smartphone. It should be understood that this embodiment is illustrative, and should not be construed as being limiting in any way.

The user device 102 can execute an operating system 106 and one or more application programs such as, for example, a location and proximity application 108 (labeled "LPA 108" in FIG. 1). The operating system 106 can include a computer program that can be configured to control the operation of the user device 102. The location and proximity application 108 can include an executable program that can be configured to execute on top of the operating system 106 to provide various functions as illustrated and described herein for using scent fingerprints and sound fingerprints for location and proximity determinations.

In particular, the location and proximity application 108 can be configured to interact with one or more sensors 110 of the user device 102 to generate sensor data 112. According to various embodiments of the concepts and technologies disclosed herein, the sensors 110 can include one or more location determination devices (e.g., global positioning system ("GPS") receivers, wireless transceivers, motion sensors, orientation sensors, and the like), one or more light sensors, one or more temperature sensors, one or more sound sensors (e.g., microphones, pressure sensors, etc.), one or more scent sensors (e.g., electronic noses or other sensors that can detect smells and/or other chemical compositions in the air, etc.), other sensors, combinations thereof, or the like.

Thus, it can be appreciated that the sensor data 112 can include, for example, geographic location information (e.g., GPS coordinates and/or other definitions of location associated with the user device 102), sound data (e.g., one or more measured frequencies in a proximity of the user device 102, measured volumes of the one or more frequencies in the proximity of the user device 102, combinations of frequencies in the proximity of the user device 102, etc.), scent data (e.g., one or more chemicals sensed in the proximity of the user device 102, concentrations of the one or more chemicals sensed in the proximity of the user device 102, combinations of chemicals in the proximity of the user device 102, etc.), movement data (e.g., information that describes movements of the user device 102, orientations of the user device 102, etc.), combinations thereof, or the like.

The sensor data 112 also can include usage data, which can capture information that describes resources being used and/or accessed by the user device 102 at a particular location (e.g., applications being executed by the user device 102, applications or services being accessed by the user device 102, data being stored and/or accessed by the user device 102, combinations thereof, or the like). The sensor data 112 also can include other data such as, for example, orientation information, device information, user information, identifiers, combinations thereof, or the like. Because the sensor data 112 can include additional and/or alternative information, it should be understood that this example is illustrative, and therefore should not be construed as being limiting in any way.

According to various embodiments of the concepts and technologies disclosed herein, the location and proximity application 108 can be configured to obtain, via the sensors 110, sensor readings that the location and proximity application 108 can compile into a data set such as the sensor data 112. According to various embodiments of the concepts and technologies disclosed herein, the user device 102 can be configured, via execution of the location and proximity application 108, to generate a new release or instance of the sensor data 112 at various times such as, for example, at time intervals (e.g., every n seconds, minutes, or the like); when movements or certain movements of the user device 102 are detected by the location and proximity application 108; on demand; when the user device 102 is determined to be in proximity of another device, location, or entity; at other times; combinations thereof; or the like. Because the sensor data 112 can be generated at additional and/or alternative times, it should be understood that these examples are illustrative, and therefore should not be construed as being limiting in any way.

According to various embodiments of the concepts and technologies disclosed herein, the location and proximity application 108 can be configured to detect a trigger (or be triggered) to generate the sensor data 112, and to access the sensors 110 to obtain sensor readings and/or data that will be included in the sensor data 112 as noted above. Thus, for example, the location and proximity application 108 can be configured to activate one or more microphones to determine one or more sounds in a proximity of the user device 102; to activate one or more scent sensors to determine one or more scents in the proximity of the user device 102; to activate a GPS receiver of the user device 102 to determine a geographic location of the user device 102; activate other sensors 110 as illustrated and described herein; or the like.

The location and proximity application 108 can obtain sensor readings and/or output from the sensors 110, and generate an instance of the sensor data 112 based on the sensor readings and/or data obtained. Thus, the sensor data 112 can include sound data, scent data, geographic location data, movement data, etc., as noted above, where the sensor data 112 is associated with one or more environments 114A-B (hereinafter collectively and/or generically referred to as "environments 114"). It should be understood that this example is illustrative, and therefore should not be construed as being limiting in any way.

The environments 114 can correspond to one or more geographic locations, one or more geographic areas, one or more buildings, and/or other locations, areas, regions, buildings, or the like. In some embodiments, for example, the environment 114A can correspond to a shopping mall, for example, and the environment 114N can correspond to an office building, for example. It should be understood that these examples are illustrative, and therefore should not be construed as being limiting in any way. As shown in FIG. 1, the user device 102 may be located at a first location $L_1$ at a first time $T_1$ in the environment 114A. The user device 102 may move over time to a different location such as the environment 114N, where the user device 102 may be located at a second location $L_2$ at a second time $T_2$ in the environment 114N. Then, the user device 102 can move within the environment 114N so that the user device 102 may be located at a third location $L_3$ at a third time $T_3$ in the environment 114N, and at a fourth location $L_4$ at a fourth time $T_4$ in the environment 114N. It should be understood that these examples are illustrative, and therefore should not be construed as being limiting in any way.

In accordance with various embodiments of the concepts and technologies disclosed herein, the user device may be configured, e.g., via execution of the location and proximity application 108, to transmit one or more instances of the sensor data 112 to another entity when a movement into, through, from, and/or between environments 114 occurs and/or are detected. Thus, in the example embodiment shown in FIG. 1, the user device 102 can be configured to transmit four instances of sensor data 112, for example at the first time $T_1$, the second time $T_2$, the third time $T_3$, and the fourth time $T_4$. It should be understood that this example is illustrative, and therefore should not be construed as being limiting in any way.

According to various embodiments of the concepts and technologies disclosed herein, the user device 102 can transmit the one or more releases or instances of the sensor data 112 to a location and proximity service 116 or other service or application. The location and proximity service 116 can correspond to a service operating on a device such as the server computer 118, where this service is configured to enable the embodiments of the concepts and technologies disclosed herein. According to various embodiments, the functionality of the server computer 118 can be provided, in some embodiments, by one or more server computers, desktop computers, laptop computers, other computing systems, and the like. It should be understood that the functionality of the server computer 118 can be provided by a single device, by two or more similar devices, and/or by two or more dissimilar devices. For purposes of describing the concepts and technologies disclosed herein, the server computer 118 is described herein as a server computer such as a web server or application server. It should be understood that this embodiment is illustrative, and should not be construed as being limiting in any way.

The location and proximity service 116 can be configured to receive the sensor data 112, and to determine, based on the sensor data 112, a location and/or proximity of the user device 102 including, an environment 114 at which and/or within which the user device 102 is located, as well as a location within the environment 114 at which the user device 102 is located. By way of example, if the environment 114 at which the user device 102 is located corresponds to a shopping mall, the location and proximity service 116 can be configured to determine, based on the sensor data 112 and/or other information as explained herein, a particular location within the shopping mall at which the user device 102 is located. It should be understood that this example is illustrative, and therefore should not be construed as being limiting in any way.

According to various embodiments of the concepts and technologies disclosed herein, the location and proximity service 116 can be configured to generate and/or store one or more fingerprints 120, which can be used to determine the proximity and/or location of the user device 102. The fingerprints 120 can include, for example, sound fingerprints 122 and scent fingerprints 124, which are described in more detail below. Because other information (e.g., geographic location data, light data, connection data, etc.) can be included in the fingerprints 120, it should be understood that these example components are illustrative and should not be construed as being limiting in any way.

A sound fingerprint 122 can include information describing one or more sounds detected using one or more of the sensors 110, and a geographic location at which the sounds were detected. Thus, the sound fingerprint 122 can be used to associate particular sounds and/or combinations of sounds with a particular geographic location.

In some embodiments, the sound fingerprints 122 can include data that describes the one or more sounds such as, for example, a frequency of the sound, a perceived intensity (e.g., volume) of the sound at that frequency, a pattern associated with the sound (e.g., a volume pattern or frequency pattern), combinations thereof, or the like. Thus, it can be appreciated that the sound fingerprints 122 can describe some or all sound perceived at a particular geographic location.

In one example embodiment, a sound fingerprint 122 can describe a first sound, a first frequency or first frequency pattern associated with the first sound, a first volume or first volume pattern associated with the first sound; a second sound, a second frequency or second frequency pattern associated with the second sound, a second volume or second volume pattern associated with the second sound; . . . ; and an nth sound, an nth frequency or nth frequency pattern associated with the nth sound, an nth volume or nth volume pattern associated with the nth sound. The sound fingerprint 122 also can include other generalized information associated with sound represented by the sound fingerprint 122 such as, for example, an average frequency, an average frequency pattern, an average volume, an overall volume, etc. Thus, it can be appreciated that the sound fingerprint 122 can describe one or more perceived sounds and/or sound levels associated with a particular geographic location. As will be explained in more detail herein, this information can be used to determine location and/or proximity based on sound.

A scent fingerprint 124 can include information describing one or more scents detected using one or more of the sensors 110, and a geographic location at which the scents were detected. Thus, the scent fingerprint 124 can be used to associate particular scents and/or combinations of scents with a particular geographic location.

In some embodiments, the scent fingerprints 124 can include data that describes the one or more scents such as, for example, a chemical makeup of the scent(s), a perceived intensity or intensities (e.g., strength(s)) of the particular scent(s), combinations thereof, or the like. Thus, it can be appreciated that the scent fingerprints 124 can describe some or all scents perceived at a particular geographic location.

In one example embodiment, a scent fingerprint 124 can describe a first scent (e.g., a first chemical makeup associated with the first scent) and a first intensity (e.g., parts per million ("PPM"), etc.) of the first scent; a second scent (e.g., a second chemical makeup associated with the second scent) and a second intensity (e.g., PPM, etc.) of the second scent; . . . ; and an nth scent (e.g., an nth chemical makeup associated with the nth scent) and an intensity (e.g., PPM, etc.) of the nth scent. The scent fingerprint 124 also can include other generalized information associated with scent represented by the scent fingerprint 124 such as, for example, a total list of chemicals among all scents detected, perceived intensities (e.g., PPM, etc.) of each of the perceived chemicals, etc. Thus, it can be appreciated that the scent fingerprint 124 can describe one or more perceived scents and/or scent intensities associated with a particular geographic location. As will be explained in more detail herein, this information can be used to determine location and/or proximity based on scent.

Thus, it can be appreciated that the fingerprints 120 can describe scents and smells associated with a particular geographic location, and therefore can be used as an accurate source of location and/or proximity data when other sensors (e.g., GPS, etc.) are unavailable. It should be understood that this example is illustrative, and therefore should not be construed as being limiting in any way.

According to various embodiments, the location and proximity service 116 can be configured to obtain the sensor data 112, and to generate a fingerprint 120 based on the sensor data 112. It can be appreciated from the above description that the fingerprints 120 generated by the location and proximity service 116 can include sound fingerprints 122, scent fingerprints 124, proximity data, location data, movement data, environment data, etc. Thus, the location and proximity service 116 can be configured to analyze the sensor data 112 and determine, based on the sensor data 112, a fingerprint 120 associated with a particular geographic location and/or area such as an environment 114 and/or a particular portion of the environments 114. The fingerprint 120 can be used to understand sounds, scents, and other aspects of various locations and/or points within and/or throughout the environments 114. It should be understood that this example is illustrative, and therefore should not be construed as being limiting in any way.

Thus, embodiments of the concepts and technologies disclosed herein can be used to create the fingerprints 120, where the fingerprints 120 can include sound fingerprints 122, scent fingerprints 124, and/or other information associated with various environments 114. According to some other embodiments of the concepts and technologies disclosed herein, the fingerprints 120 can be used to determine location and/or proximity of the user device 102 and/or other devices within the environments 114, and/or for other purposes such as, for example, to trigger various actions and/or to provide services based on the location and/or proximity of the user device 102 within the environments 114. It should be understood that this example is illustrative, and therefore should not be construed as being limiting in any way.

In particular, in some embodiments of the concepts and technologies disclosed herein, the location and proximity service 116 can be configured to obtain, from the user device 102, one or more releases of sensor data 112. The location and proximity service 116 can be configured to use the sensor data 112 to create the fingerprints 120, as noted above, and/or to use the fingerprints 120 to determine if actions should be triggered based on a location and/or proximity of the user device 102. Thus, releases of the sensor data 112 can be viewed, in some instances, as a request for the location and proximity service 116 to use the fingerprints 120 to determine if an action should be triggered and/or if services should be offered based on locations and/or proximities of the user device 102, in some embodiments.

Thus, for example, the location and proximity service 116 can be configured to detect a movement of a user device 102 into, within, out of, between, and/or otherwise with respect to or relative to one or more environments 114. For example, as shown in FIG. 1, the location and proximity service 116 can be configured to detect a movement of the user device 102 through and/or out of the environment 114A, between the environment 114A and the environment 114N, into the environment 114N, within the environment 114N, out of the environment 114N, or the like. In response to detecting the movement of the user device 102, the location and proximity service 116 can be configured to determine if the user device 102 has opted-in to using scent fingerprints and/or sound fingerprints to determine location and/or proximity. The location and proximity service 116 can determine that the user device 102 has opted-in or not opted-in based on preferences, settings, and/or other information that can convey the decision associated with the user device 102 for opting-in and/or opting-out. In some other embodiments, the location and proximity service 116 can send, to the user device 102, a request to opt-in or opt-out of using sound and/or scent for making location and/or proximity determinations at any time. Thus, it should be understood that these examples are illustrative, and therefore should not be construed as being limiting in any way.

If the user device 102 or a user associated with the user device 102 has opted-in to using scent and/or sound for location and/or proximity determinations, the location and proximity service 116 can be determined to determine if a fingerprint 120 associated with the user device 102 is stored and/or is accessible to the location and proximity service 116. Thus, for example, the location and proximity service 116 can search the fingerprints 120 to determine if a fingerprint 120 associated with the user device 102 and/or a geographic location is stored and/or is accessible to the location and proximity service 116. As such, it can be appreciated that the fingerprints 120 can include location data that can be used to search for locations; user and/or device data that can be used to search for particular devices and/or users; and/or other data as illustrated and described herein for determining if a fingerprint 120 associated with a device, user, and/or location is accessible and/or is stored. It should be understood that these examples are illustrative, and therefore should not be construed as being limiting in any way.

If the location and proximity service 116 determines that a fingerprint 120 associated with the user device 102 and/or the geographic location (e.g., the environments 114) is accessible to the location and proximity service 116, the location and proximity service 116 can retrieve the fingerprint 120 for use. If the location and proximity service 116 determines that a fingerprint 120 associated with the user device 102 and/or the geographic location (e.g., the environments 114) is not accessible to the location and proximity service 116, the location and proximity service 116 can use a release of the sensor data 112 to create the fingerprint 120, in some embodiments. Because the location and proximity service 116 can take other actions if it is determined that the fingerprint 120 associated with the user device 102 and/or the location is not stored by and/or accessible to the location and proximity service 116, it should be understood that this example is illustrative, and therefore should not be construed as being limiting in any way.

The location and proximity service 116 can create the fingerprint 120 by commanding the user device 102 (e.g., via communications with the location and proximity application 108) to capture location, proximity, scent, sound, and/or other information, and to submit instances of that information to the location and proximity service 116 as the sensor data 112, for example. According to various embodiments, the location and proximity service 116 can perform recognition on the sensor data 112 to determine sound fingerprints 122 and/or scent fingerprints 124 at locations and/or points within locations associated with the user device 102. The location and proximity service 116 also can determine, based on the sensor data 112, locations of the user device 102 at various times. For purposes of creating the fingerprints 120, the location determined by the location and proximity service 116 can also include movements and/or proximities of the user device 102. For example, the if the environment 114 in which the user device 102 is moving is a shopping mall, the shopping mall can include location beacons and/or other devices for tracking movements and/or orientation of the user device 102 within the environment 114. Thus, as the user device 102 captures the sensor data 112, location and/or proximity information for the user device 102 can also be captured, e.g., from the user device 102 and/or from other devices that can communicate with the location and proximity service 116.

The location and proximity service 116 can be configured to record and store the fingerprint 120 based on the release of sensor data 112. Therefore, as noted herein, the fingerprint 120 can include a sound fingerprint 122 for a particular location and/or proximity; a scent fingerprint 124 for a particular location and/or proximity; geographic location information, proximity information, and/or orientation information for a particular location and/or proximity; combinations thereof; or the like. The location and proximity service 116 can create and store the fingerprint 120 for immediate and/or future use.

Regardless of when the fingerprint 120 is used (e.g., either immediately after creation and/or later after retrieval), the fingerprint 120 can be used in association with sensor data 112 to determine, based on scents, sounds, locations, and/or other information represented by the sensor data 112, if an action should be taken. In particular, the fingerprint 120 can be used by the location and proximity service 116 to determine a location and/or proximity of the user device 102. For example, if a fingerprint 120 indicates that at a specific location and/or proximity, sounds (e.g., as defined in a sound fingerprint 122 associated with the location and/or proximity) and scents (e.g., as defined in a scent fingerprint 124 associated with the location and/or proximity) will be detected. Thus, the location and proximity service 116 can determine, based on sounds and/or scents captured by sensor data 112, where the user device 102 is located and/or what is in a proximity of the user device 102 without capturing other location information and/or proximity information with the sensor data 112. It should be understood that this example is illustrative, and therefore should not be construed as being limiting in any way.

The location and proximity service 116 can obtain another release of sensor data 112 at some time, and determine, based on the fingerprint 120 and the new release of the sensor data 112, if an action should be taken based on a location and/or proximity of the user device 102. If the location and proximity service 116 determines that an action should be taken, the location and proximity service 116 can trigger the action. In some embodiments, the action can include instantiating and/or orchestrating a service or resource. For example, the location and proximity service 116 can be configured to generate a command 126 that, when received by a device such as the computing device 128, causes the computing device 128 to create or obtain a resource 130, or otherwise to make the resource available to the user device 102.

Other actions that can be taken can include triggering delivery of advertisements or other information; commanding the user device 102 to launch a particular application (e.g., an authentication application, a particular application for accessing the resource 130, etc.); or the like. Thus, while the command 126 is illustrated as being transmitted to the computing device 128, it should be understood that the location and proximity service 116 can also send one or more commands 126 to the user device 102. It should be understood that this example is illustrative, and therefore should not be construed as being limiting in any way. Thus, it can be appreciated that scent and sound can be used to determine a location and/or proximity of the user device 102, and to trigger various actions based on the determined location and/or proximity.

In practice, a user device 102 can move into, through, out of, and/or between one or more environments 114 or other locations. The user device 102 can generate, using one or more sensors 110, an instance of sensor data 112 that can be provided to a server computer 118. The server computer 118 can be configured, e.g., via execution of a location and proximity service 116, to generate, based on the sensor data 112, a fingerprint 120 that describes sounds and smells associated with one or more geographic locations and/or proximities of the user device 102 (e.g., devices and/or entities in a proximity of the user device 102). The fingerprint 120 can be stored or immediately used for various purposes.

In particular, the server computer 118 can be configured to detect a movement of the user device 102 relative to an environment 114, and to determine if a user or other entity associated with the user device 102 has opted in to, or opted out from, using scent and/or sound to determine location and/or proximity. In some embodiments, the user device 102 can be queried for an opt-in/opt-out decision by the location and proximity service 116 (e.g., at setup time and/or at any other time), while in some other embodiments the user device 102 can define opt-in and/or opt-out preferences at the user device 102 (e.g., during installation, activation, and/or configuration of the location and proximity application 108). Because the opt-in and/or opt-out decision can be obtained from the user device 102 in additional and/or alternative manners, it should be understood that these examples are illustrative, and therefore should not be construed as being limiting in any way.

If the user device 102 has opted-in to use scent and sound for determining location and/or proximity, the location and proximity service 116 can be configured to determine if a fingerprint 120 is stored for the user device 102 and/or the associated location relative to which the movement was detected. If a fingerprint 120 is not stored and/or accessible, the location and proximity service 116 can be configured to create a fingerprint 120. If a fingerprint 120 is stored and/or is accessible, the location and proximity service 116 can obtain the fingerprint associated with the user device 102 and the location, as well as an additional release of the sensor data 112.

The location and proximity service 116 can compare the additional release of the sensor data 112 to the fingerprint 120 to determine where the user device 102 is located. Namely, the sound and/or scent information from the sensor data 112 can be compared to the sound fingerprint 122 and/or scent fingerprint 124 in the fingerprint 120 to determine a relative location of the user device 102 to the location and/or proximity captured by the fingerprint 120. It can be appreciated that multiple fingerprints 120 can be used to determine where the user device 102 is located, based on sound and/or scent information, among other data.

Upon determining a location and/or proximity of the user device 102, the location and proximity service 116 can determine if an action should be taken. Namely, the fingerprints 120 can also define, for specific locations, scent fingerprints, sound fingerprints, proximities, and the like, resources 130 that were accessed and/or used by the user device 102. Thus, for example, the fingerprint 120 can define, for a particular location and device, one or more applications being used at the user device 102; one or more resources 130 being accessed by the user device 102; a sound fingerprint at the user device 102; a scent fingerprint at the user device 102; combinations thereof; or the like. Thus, the fingerprints 120 can be used to determine location and proximity, and also to determine resources 130 accessed and/or used by the user device 102 at the various locations and/or proximities. It should be understood that this example is illustrative, and therefore should not be construed as being limiting in any way.

If the location and proximity service 116 determines that an action should be taken (or triggered), the location and proximity service 116 can generate one or commands 126 for taking or triggering the action. Thus, for example, the location and proximity service 116 can generate a command 126 that, when received by the computing device 128, causes the computing device 128 to host a resource 130, make the resource 130 available, activate a service, or otherwise make the resource 130 available to the user device 102. The command 126 also can include instructions that, when received by the user device 102, causes the user device 102 to activate or access a resource such as the resource 130, an application installed at the user device 102, and/or other resources. The location and proximity service 116 can update the fingerprint 120 to reflect the most recent use, in some embodiments. It should be understood that this example is illustrative, and therefore should not be construed as being limiting in any way.

FIG. 1 illustrates one user device 102, one network 104, two environments 114, and one server computer 118. It should be understood, however, that various implementations of the operating environment 100 can include zero, one, or more than one user device 102; zero, one, or more than one network 104; one, two, or more than two environments 114; and/or zero, one, or more than one server computer 118. As such, the illustrated embodiment should be understood as being illustrative, and should not be construed as being limiting in any way.

Figure 2:
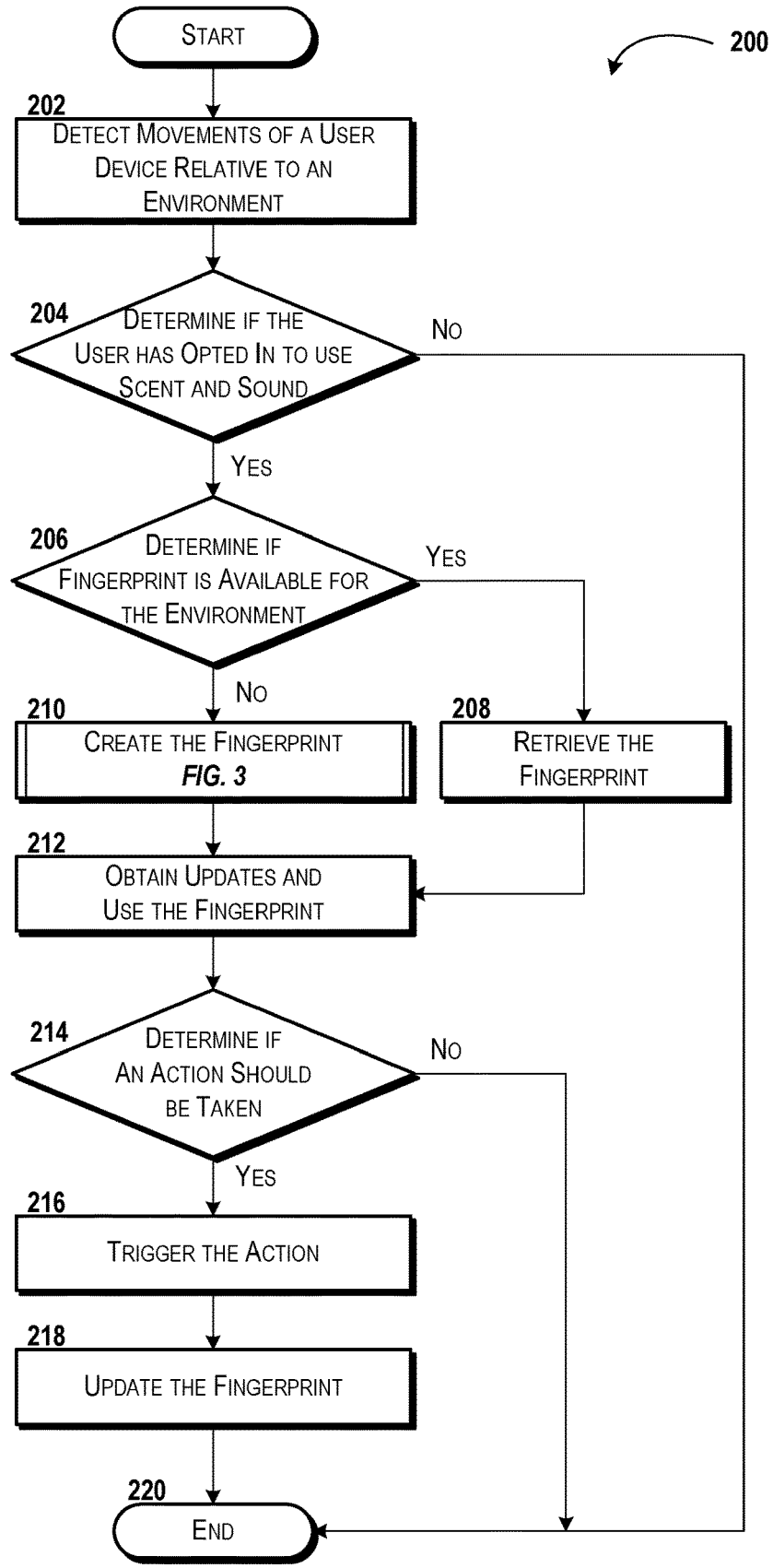
FIG. 2 is a flow diagram showing aspects of a method for using scent fingerprints and sound fingerprints for location and proximity determinations, according to an illustrative embodiment of the concepts and technologies described herein.

Turning now to FIG. 2, aspects of a method 200 for using scent fingerprints 124 and sound fingerprints 122 for location and proximity determinations will be described in detail, according to an illustrative embodiment. It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the concepts and technologies disclosed herein.

It also should be understood that the methods disclosed herein can be ended at any time and need not be performed in its entirety. Some or all operations of the methods, and/or substantially equivalent operations, can be performed by execution of computer-readable instructions included on a computer storage media, as defined herein. The term "computer-readable instructions," and variants thereof, as used herein, is used expansively to include routines, applications, application modules, program modules, programs, components, data structures, algorithms, and the like. Computer-readable instructions can be implemented on various system configurations including single-processor or multiprocessor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof. As used herein, the phrase "cause a processor to perform operations" and variants thereof is used to refer to causing a processor of a computing system or device, such as the user device 102 and/or the server computer 118, to perform one or more operations and/or causing the processor to direct other components of the computing system or device to perform one or more of the operations.

For purposes of illustrating and describing the concepts of the present disclosure, the method 200 is described herein as being performed by the server computer 118 via execution of one or more software modules such as, for example, the location and proximity service 116. It should be understood that additional and/or alternative devices and/or network nodes can provide the functionality described herein via execution of one or more modules, applications, and/or other software including, but not limited to, the location and proximity service 116. Thus, the illustrated embodiments are illustrative, and should not be viewed as being limiting in any way.

The method 200 begins at operation 202. At operation 202, the server computer 118 can detect a movement of a user device 102 relative to an environment such as, for example, one of the environments 114. It should be understood that the functionality of operation 202 can be provided by the server computer 118 detecting movement of a user device 102 into one or more environment 114, movement of a user device 102 within one or more environment 114, movement of a user device 102 out of one or more environment 114, combinations thereof, or the like. According to various embodiments of the concepts and technologies disclosed herein, the server computer 118 can detect the movement in operation 202 by obtaining a release of the sensor data 112 and determining, based on an analysis of the sensor data 112, that the user device 102 has moved into, within, out of, and/or between one or more environments 114. Because the movements can be detected in operation 202 in additional and/or alternative manners, it should be understood that this example is illustrative, and therefore should not be construed as being limiting in any way.

From operation 202, the method 200 can proceed to operation 204. At operation 204, the server computer 118 can determine if a user (e.g., the user associated with the user device 102) has opted in to use scent and/or sound for location and proximity determinations. According to various embodiments of the concepts and technologies disclosed herein, a user or other entity associated with the user device 102 can opt-in or opt-out of using scent and/or sound for location and/or proximity determinations during installation, activation, and/or use of the location and proximity application 108; during registration and/or setup with the location and proximity service 116; when a release of sensor data 112 is obtained by the location and proximity service 116; on demand; and/or at other times.

As such, the functionality of the server computer 118 illustrated and described with respect to operation 204 can include determining if an opt-in or opt-out decision exists for the user device 102, sending an opt-in decision query (e.g., an opt-in/opt-out screen) to the user device 102, and/or otherwise determining if the user device 102 is opted-in or opted-out for location and/or proximity determinations using scent and/or sound. Because the determination of operation 204 can be made in additional and/or alternative manners, it should be understood that these examples are illustrative, and therefore should not be construed as being limiting in any way.

If the server computer 118 determines, in operation 204, that a user associated with the user device 102 has opted in to use scent and/or sound for location and proximity determinations, the method 200 can proceed to operation 206. At operation 206, the server computer 118 can determine if one or more fingerprints 120 are stored for the environment 114 associated with the movement detected in operation 202. It should be understood that the functionality of operation 204 can also include determining that a fingerprint 120 for the environment 114 is also associated with the user device 102 associated with the opt-in determined to exist (or not exist) in operation 204. Thus, in operation 206, the server computer 118 can determine if a fingerprint 120 for the user device 102 and the environment 114 exist and/or is stored. It should be understood that this example is illustrative, and therefore should not be construed as being limiting in any way.

If the server computer 118 determines, in operation 206, that one or more fingerprints 120 are stored for the environment 114 and the user device 102 associated with the movement detected in operation 202, the method 200 can proceed to operation 208. At operation 208, the server computer 118 can retrieve one or more of the fingerprints 120 that are stored for the environment 114 associated with the movement detected in operation 202. As explained above, the fingerprints 120 can be stored with information that can associate the fingerprints 120 with particular user devices (e.g., the user device 102), particular users (e.g., a user of the user device 102), particular locations and/or proximities, etc. Thus, the fingerprints 120 can be keyed on multiple data in the fingerprints 120 and therefore can be retrieved based on any data included in the fingerprints 120, in some embodiments.

If the server computer 118 determines, in operation 206, that one or more fingerprints 120 are not stored for the environment 114 and the user device 102 associated with the movement detected in operation 202, the method 200 can proceed to operation 210. At operation 210, the server computer 118 can create one or more fingerprints 120 for the environment 114 associated with the movement detected in operation 202. More details of the operations for creating the fingerprints 120 are illustrated and described herein with reference to FIG. 3, but it should be noted at least that a release or instance of sensor data 112 can be obtained by the server computer 118 to create the fingerprint 120, in some embodiments. It should be understood that this example is illustrative, and therefore should not be construed as being limiting in any way.

From operation 210, the method 200 can proceed to operation 212. The method 200 also can proceed to operation 212 from operation 208. At operation 212, the server computer 118 can obtain updates to the sensor data 112 and use the fingerprint 120 retrieved in operation 208 or created in operation 210. Thus, in operation 212 the server computer 118 can obtain one or more additional releases and/or instances of the sensor data 112, which can include one or more updates to a location of the user device 102, a proximity of the user device 102, one or more scents at or near the user device 102, one or more sounds at or near the user device 102, one or more movements and/or orientations of the user device 102, combinations thereof, or the like. In another embodiment, the server may occasionally re-compute a fingerprint (e.g., as determined by a low confidence score from a retrieval system or other device, a fixed time interval, a new user or sensor detected, etc.) for an environment 114 to validate that its fingerprint is still accurate and correctly characterizes the sensor data 112. It should be understood that this example is illustrative, and therefore should not be construed as being limiting in any way.

In operation 214, the server computer 118 also can use the fingerprint 120 retrieved in operation 208 and/or created in operation 210, in association with the updated sensor data 112, to determine a location and/or proximity of the user device 102. As explained above, the uniqueness of the sound fingerprints 122 and the scent fingerprints 124 can be leveraged by embodiments of the concepts and technologies disclosed herein to use scent and sound to determine location and/or proximity of the user device 102. Thus, the new release of the sensor data 112 can be compared to the fingerprint 120 to determine a location and/or proximity of the user device 102. It should be understood that this example is illustrative, and therefore should not be construed as being limiting in any way.

From operation 212, the method 200 can proceed to operation 214. At operation 214, the server computer 118 can determine if an action should be triggered and/or taken, e.g., based on the location and/or proximity of the user device 102 as determined using the fingerprint 120 and the movements in the environment 114 as depicted by the sensor data 112 update obtained in operation 212. It should be understood that this example is illustrative, and therefore should not be construed as being limiting in any way.

As noted above, the action can include, for example, the location and proximity service 116 can be configured to create and/or make available certain resources 130 to the user device 102 based on the location and/or proximity of the user device 102; to cause the user device 102 to activate, install, and/or use a particular application based on the location and/or proximity of the user device 102; to send particular data and/or reports to one or more other devices; to cause other devices to install and/or make available the resource 130; combinations thereof; or the like. In some embodiments, the determination of operation 214 can be made based on determining that when previously in a particular location, the user device 102 used and/or accessed a particular resource 130. In some other embodiments, the determination of operation 214 can be made based on determining that when previously in location with a similar sound and smell (to the current sound and smell), the user device 102 used and/or accessed a particular resource 130, and deciding that the user device 102 may be interested in the same resource 130 based on the sound and smell being similar. It should be understood that this example is illustrative, and therefore should not be construed as being limiting in any way.

If the server computer 118 determines, in operation 214, that an action should be taken based on the fingerprint 120 and the movements of the user device 102 in the environment 114, the method 200 can proceed to operation 216. At operation 216, the server computer 118 can trigger one or more actions as determined in operation 214. Thus, for example, the server computer 118 can generate one or more commands 126 that, when received by the computing device 128, cause the computing device 128 to make a resource 130 available to the user device 102. Thus, it can be appreciated that the resource 130 can include an application or service that can be installed and/or activated by the command 126; data that can be loaded to and/or made available by the computing device 128; or the like. In some other embodiments, the commands 126 can cause the user device 102 to access and/or obtain the resource 130, and/or to take other actions to share or obtain data as illustrated and described herein. Because other actions can be triggered by the server computer 118, it should be understood that these examples are illustrative, and therefore should not be construed as being limiting in any way.

From operation 216, the method 200 can proceed to operation 218. At operation 218, the server computer 118 can update the fingerprint 120 retrieved in operation 208 or created in operation 210 based on the action taken in operation 216. Thus, the fingerprint 120 can be updated with additional information to depict services and/or other resources 130 that should be installed and/or made available based on movements of the user device 102; applications at the user device 102 that should be activated at certain locations and/or proximities; and/or other actions.

It can be appreciated that the actions taken by the server computer 118 can be triggered at other devices (e.g., the computing device 128 and/or the user device 102, for example), in some embodiments, while in some other embodiments the actions can be triggered and/or taken at the server computer 118. Thus, the illustrated embodiment should be understood as being illustrative and should not be construed as being limiting in any way. Thus, operation 218 can include updating the fingerprint 120 to reflect actions taken at various locations, in some embodiments. It should be understood that this example is illustrative, and therefore should not be construed as being limiting in any way.

From operation 218, the method 200 can proceed to operation 220. The method 200 also can proceed to operation 220 if the server computer 118 determines, in operation 214, that an action should not be taken based on the fingerprint 120 and the movements in the environment 114. The method 200 also can proceed to operation 220 from operation 204 if the server computer 118 determines, in operation 204, that if a user (associated with the user device 102) has not opted in to use scent and sound for location and proximity determinations. The method 200 can end at operation 220.

Figure 3:
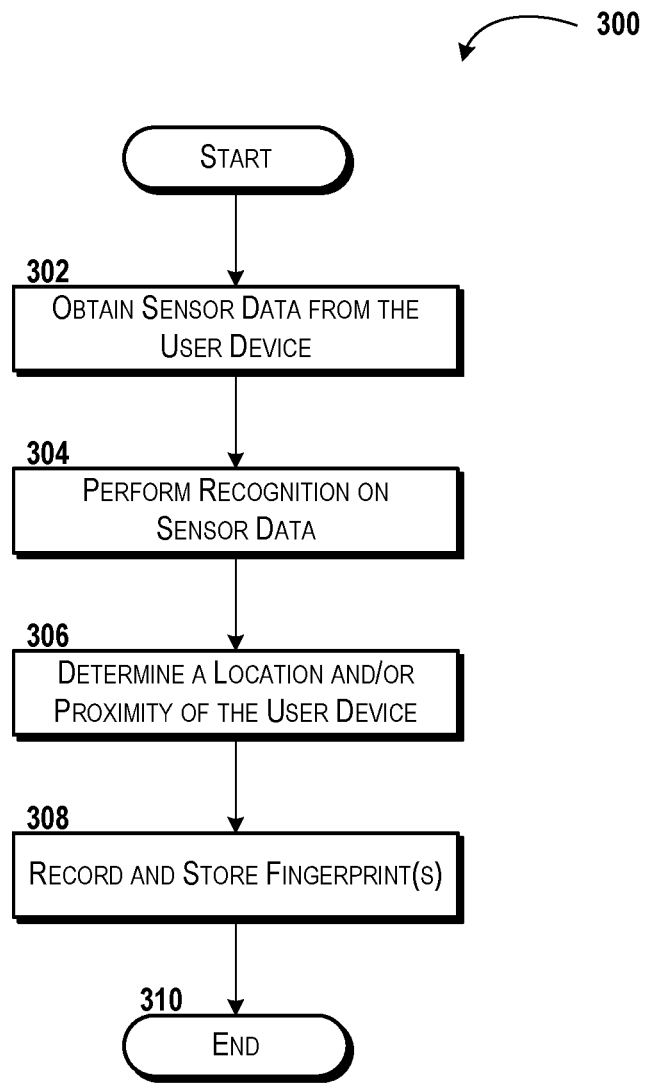
FIG. 3 is a flow diagram showing aspects of a method for creating scent fingerprints and sound fingerprints, according to an illustrative embodiment of the concepts and technologies described herein.

Turning now to FIG. 3, aspects of a method 300 for creating scent fingerprints and sound fingerprints will be described in detail, according to an illustrative embodiment. For purposes of illustrating and describing the concepts of the present disclosure, the method 300 is described herein as being performed by the server computer 118 via execution of one or more software modules such as, for example, the location and proximity service 116. It should be understood that additional and/or alternative devices and/or network nodes can provide the functionality described herein via execution of one or more modules, applications, and/or other software including, but not limited to, the location and proximity service 116. Thus, the illustrated embodiments are illustrative, and should not be viewed as being limiting in any way.

The method 300 begins at operation 302. At operation 302, the server computer 118 can obtain an instance or release of sensor data 112. In some embodiments of the concepts and technologies disclosed herein, the server computer 118 can perform operation 302 by sending, to the user device 102, a command to send a release of the sensor data 112 to the server computer 118. In some other embodiments of the concepts and technologies disclosed herein, the server computer 118 can receive or otherwise obtain a release of the sensor data 112 from the user device 102 without requesting the sensor data 112 and/or without commanding the user device 102 to send the sensor data 112, e.g., the user device 102 can send the sensor data 112 to the server computer 118 without a request or command 126. Because the sensor data 112 can be obtained by the server computer 118 at additional and/or alternative times, it should be understood that these examples are illustrative, and therefore should not be construed as being limiting in any way.

From operation 302, the method 300 can proceed to operation 304. At operation 304, the server computer 118 can perform recognition on the sensor data 112 obtained in operation 302. Operation 304 can include the server computer 118 analyzing the release of the sensor data 112 to determine a location of the user device 102, a proximity of a user device 102 (e.g., a proximity of the user device 102 to another device or entity and/or other devices or entities in a specified range/proximity of the user device 102 such as a ten foot radius, etc.), sounds detected in the proximity of the user device 102, scents detected in the proximity of the user device 102, and/or other information such as a temperature in the proximity of the user device 102, light levels in the proximity of the user device 102, combinations thereof, or the like.

In various embodiments of the concepts and technologies disclosed herein, operation 304 includes at least the server computer 118 determining, based on the release of the sensor data 112 obtained in operation 302, a) a geographic location of the user device 102; b) determining devices and/or other entities in a proximity of the user device 102; c) one or more sounds in the proximity of the user device 102; and d) one or more scents in the proximity of the user device 102. Because other information can be determined based on analysis of the sensor data 112, it should be understood that these examples are illustrative, and therefore should not be construed as being limiting in any way. Additionally, some embodiments of operation 304 can include updates based on available sensor data 112.

For example, while one fingerprint recognition may be representative of a flower's scent in the morning (e.g., a dew-like fragrance that is sharp and cool), the same scent and location may be slightly altered in its chemical makeup and interpretation (e.g., a warm blend of the fragrance and humidity) at a time later in the day. Subsequently, operation 304 may also include mechanisms for updating the original recognition operation or augmenting the recognition operation with an additional fingerprint data that can indicate the same location and proximity but based on slightly different sensor data 112. It should be understood that this example is illustrative, and therefore should not be construed as being limiting in any way.

From operation 304, the method 300 can proceed to operation 306. At operation 306, the server computer 118 can determine a location and/or proximity of the user device 102. In some embodiments, the location and/or proximity (e.g., devices at and/or near the user device 102 and/or a specific orientation of the user device 102 relative to other devices or entities) can be determined through the analysis of operation 304. In some other embodiments, the server computer 118 may obtain location and/or proximity information in operation 306 from other devices. Regardless of how they are determined, operations 304-306 can include the server computer 118 determining the location of the user device 102, the proximity of the user device 102 to other devices, sounds at or near the user device 102, and/or scents at or near the user device 102. It should be understood that this example is illustrative, and therefore should not be construed as being limiting in any way.

From operation 306, the method 300 can proceed to operation 308. At operation 308, the server computer 118 can record and store one or more fingerprints 120. Thus, operation 308 can include the server computer 118 generating a data record and/or a tuple for a database, or the like, where the data record indicates a) a device with which the record is associated (e.g., the user device 102); b) a location with which the record is associated (e.g., one of the environments 114); c) a proximity associated with the user device 102 (e.g., one or more devices and/or entities in a proximity of the user device 102); d) one or more sounds detected at the location and/or proximity; and e) one or more scents detected at the location and/or proximity.

This data can be stored as a fingerprint and retrieved for various uses as illustrated and described herein. In another embodiment, the same fingerprint (e.g., scent sensor data 112 for "new car smell") from a first environment 114 (e.g., car rental agency number one) may be associated with a second environment 114 (e.g., car rental agency number two) but with different location and/or proximity data. In some embodiments, this data record can be accommodated simply via a second tuple in a database with appropriate differing field values (e.g., only location field of five tuple fields). It should be understood that this example is illustrative, and therefore should not be construed as being limiting in any way.

From operation 308, the method 300 can proceed to operation 310. The method 300 can end at operation 310.

Figure 4:
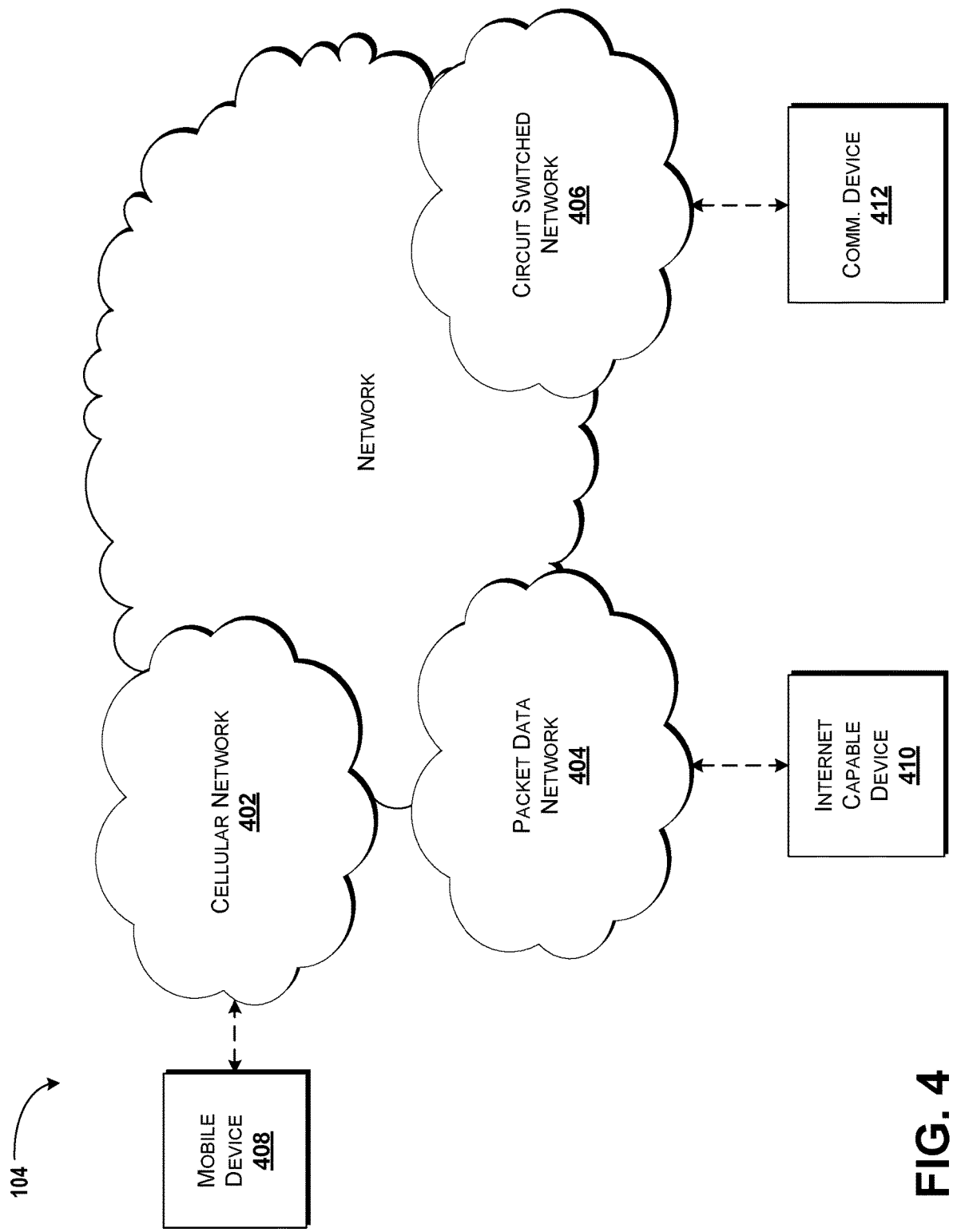
FIG. 4 schematically illustrates a network, according to an illustrative embodiment of the concepts and technologies described herein.

Turning now to FIG. 4, additional details of the network 104 are illustrated, according to an illustrative embodiment. The network 104 includes a cellular network 402, a packet data network 404, for example, the Internet, and a circuit switched network 406, for example, a publicly switched telephone network ("PSTN"). The cellular network 402 includes various components such as, but not limited to, base transceiver stations ("BTSs"), Node-B's or e-Node-B's, base station controllers ("BSCs"), radio network controllers ("RNCs"), mobile switching centers ("MSCs"), mobile management entities ("MMEs"), short message service centers ("SMSCs"), multimedia messaging service centers ("MMSCs"), home location registers ("HLRs"), home subscriber servers ("HSSs"), visitor location registers ("VLRs"), charging platforms, billing platforms, voicemail platforms, GPRS core network components, location service nodes, an IP Multimedia Subsystem ("IMS"), and the like. The cellular network 402 also includes radios and nodes for receiving and transmitting voice, data, and combinations thereof to and from radio transceivers, networks, the packet data network 404, and the circuit switched network 406.

A mobile communications device 408, such as, for example, a cellular telephone, a user equipment, a mobile terminal, a PDA, a laptop computer, a handheld computer, and combinations thereof, can be operatively connected to the cellular network 402. The cellular network 402 can be configured as a 2G GSM network and can provide data communications via GPRS and/or EDGE. Additionally, or alternatively, the cellular network 402 can be configured as a 3G UMTS network and can provide data communications via the HSPA protocol family, for example, HSDPA, EUL (also referred to as HSDPA), and HSPA+. The cellular network 402 also is compatible with 4G mobile communications standards, 5G mobile communications standards, other mobile communications standards, and evolved and future mobile communications standards.

The packet data network 404 includes various devices, for example, servers, computers, databases, and other devices in communication with one another, as is generally known. The packet data network 404 devices are accessible via one or more network links. The servers often store various files that are provided to a requesting device such as, for example, a computer, a terminal, a smartphone, or the like. Typically, the requesting device includes software (a "browser") for executing a web page in a format readable by the browser or other software. Other files and/or data may be accessible via "links" in the retrieved files, as is generally known. In some embodiments, the packet data network 404 includes or is in communication with the Internet. The circuit switched network 406 includes various hardware and software for providing circuit switched communications. The circuit switched network 406 may include, or may be, what is often referred to as a plain old telephone system (POTS). The functionality of a circuit switched network 406 or other circuit-switched network are generally known and will not be described herein in detail.

The illustrated cellular network 402 is shown in communication with the packet data network 404 and a circuit switched network 406, though it should be appreciated that this is not necessarily the case. One or more Internet-capable devices 410, for example, a PC, a laptop, a portable device, or another suitable device, can communicate with one or more cellular networks 402, and devices connected thereto, through the packet data network 404. It also should be appreciated that the Internet-capable device 410 can communicate with the packet data network 404 through the circuit switched network 406, the cellular network 402, and/or via other networks (not illustrated).

As illustrated, a communications device 412, for example, a telephone, facsimile machine, modem, computer, or the like, can be in communication with the circuit switched network 406, and therethrough to the packet data network 404 and/or the cellular network 402. It should be appreciated that the communications device 412 can be an Internet-capable device, and can be substantially similar to the Internet-capable device 410. In the specification, the network 104 is used to refer broadly to any combination of the networks 402, 404, 406. It should be appreciated that substantially all of the functionality described with reference to the network 104 can be performed by the cellular network 402, the packet data network 404, and/or the circuit switched network 406, alone or in combination with other networks, network elements, and the like.

Figure 5:
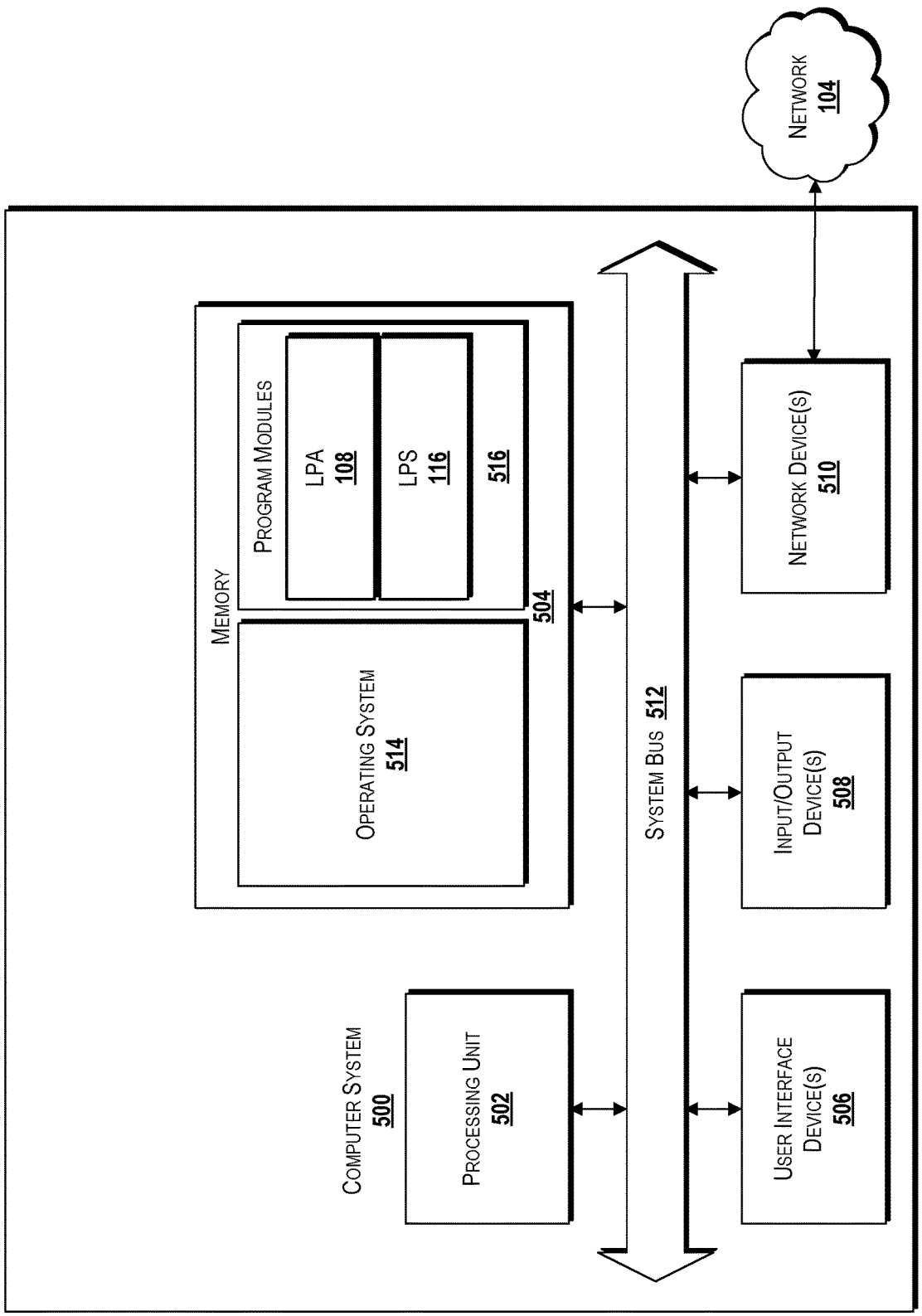
FIG. 5 is a block diagram illustrating an example computer system configured to enable using scent fingerprints and sound fingerprints for location and proximity determinations, according to some illustrative embodiments of the concepts and technologies described herein.

FIG. 5 is a block diagram illustrating a computer system 500 configured to provide the functionality described herein for using scent fingerprints and sound fingerprints for location and proximity determinations, in accordance with various embodiments of the concepts and technologies disclosed herein. The computer system 500 includes a processing unit 502, a memory 504, one or more user interface devices 506, one or more input/output ("I/O") devices 508, and one or more network devices 510, each of which is operatively connected to a system bus 512. The bus 512 enables bi-directional communication between the processing unit 502, the memory 504, the user interface devices 506, the I/O devices 508, and the network devices 510.

The processing unit 502 may be a standard central processor that performs arithmetic and logical operations, a more specific purpose programmable logic controller ("PLC"), a programmable gate array, or other type of processor known to those skilled in the art and suitable for controlling the operation of the server computer. As used herein, the word "processor" and/or the phrase "processing unit" when used with regard to any architecture or system can include multiple processors or processing units distributed across and/or operating in parallel in a single machine or in multiple machines. Furthermore, processors and/or processing units can be used to support virtual processing environments. Processors and processing units also can include state machines, application-specific integrated circuits ("ASICs"), combinations thereof, or the like. Because processors and/or processing units are generally known, the processors and processing units disclosed herein will not be described in further detail herein.

The memory 504 communicates with the processing unit 502 via the system bus 512. In some embodiments, the memory 504 is operatively connected to a memory controller (not shown) that enables communication with the processing unit 502 via the system bus 512. The memory 504 includes an operating system 514 and one or more program modules 516. The operating system 514 can include, but is not limited to, members of the WINDOWS, WINDOWS CE, and/or WINDOWS MOBILE families of operating systems from MICROSOFT CORPORATION, the LINUX family of operating systems, the SYMBIAN family of operating systems from SYMBIAN LIMITED, the BREW family of operating systems from QUALCOMM CORPORATION, the MAC OS, iOS, and/or LEOPARD families of operating systems from APPLE CORPORATION, the FREEBSD family of operating systems, the SOLARIS family of operating systems from ORACLE CORPORATION, other operating systems, and the like.

The program modules 516 may include various software and/or program modules described herein. In some embodiments, for example, the program modules 516 include the location and proximity application 108 and/or the location and proximity service 116. These and/or other programs can be embodied in computer-readable media containing instructions that, when executed by the processing unit 502, perform one or more of the methods 200, 300 described in detail above with respect to FIGS. 2-3 and/or other functionality as illustrated and described herein. It can be appreciated that, at least by virtue of the instructions embodying the methods 200, 300, and/or other functionality illustrated and described herein being stored in the memory 504 and/or accessed and/or executed by the processing unit 502, the computer system 500 is a special-purpose computing system that can facilitate providing the functionality illustrated and described herein. According to embodiments, the program modules 516 may be embodied in hardware, software, firmware, or any combination thereof. Although not shown in FIG. 5, it should be understood that the memory 504 also can be configured to store the sensor data 112; the fingerprints 120 and/or components thereof such as, for example, the sound fingerprints 122 and/or the scent fingerprints 124; and/or other data, if desired.

By way of example, and not limitation, computer-readable media may include any available computer storage media or communication media that can be accessed by the computer system 500. Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Computer storage media includes only non-transitory embodiments of computer readable media as illustrated and described herein. Thus, computer storage media can include volatile and non-volatile, removable and non-removable media implemented in any method or technology for storage of information such as computer-readable instructions, data structures, program modules, or other data. Computer storage media includes, but is not limited to, RAM, ROM, Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the computer system 500. In the claims, the phrase "computer storage medium" and variations thereof does not include waves or signals per se and/or communication media.

The user interface devices 506 may include one or more devices with which a user accesses the computer system 500. The user interface devices 506 may include, but are not limited to, computers, servers, personal digital assistants, cellular phones, or any suitable computing devices. The I/O devices 508 enable a user to interface with the program modules 516. In one embodiment, the I/O devices 508 are operatively connected to an I/O controller (not shown) that enables communication with the processing unit 502 via the system bus 512. The I/O devices 508 may include one or more input devices, such as, but not limited to, a keyboard, a mouse, or an electronic stylus. Further, the I/O devices 508 may include one or more output devices, such as, but not limited to, a display screen or a printer.

The network devices 510 enable the computer system 500 to communicate with other networks or remote systems via a network, such as the network 104. Examples of the network devices 510 include, but are not limited to, a modem, a radio frequency ("RF") or infrared ("IR") transceiver, a telephonic interface, a bridge, a router, or a network card. The network 104 may include a wireless network such as, but not limited to, a Wireless Local Area Network ("WLAN") such as a WI-FI network, a Wireless Wide Area Network ("WWAN"), a Wireless Personal Area Network ("WPAN") such as BLUETOOTH, a Wireless Metropolitan Area Network ("WMAN") such as a WiMAX network, or a cellular network. Alternatively, the network 104 may be a wired network such as, but not limited to, a Wide Area Network ("WAN") such as the Internet, a Local Area Network ("LAN") such as the Ethernet, a wired Personal Area Network ("PAN"), or a wired Metropolitan Area Network ("MAN").

Figure 6:
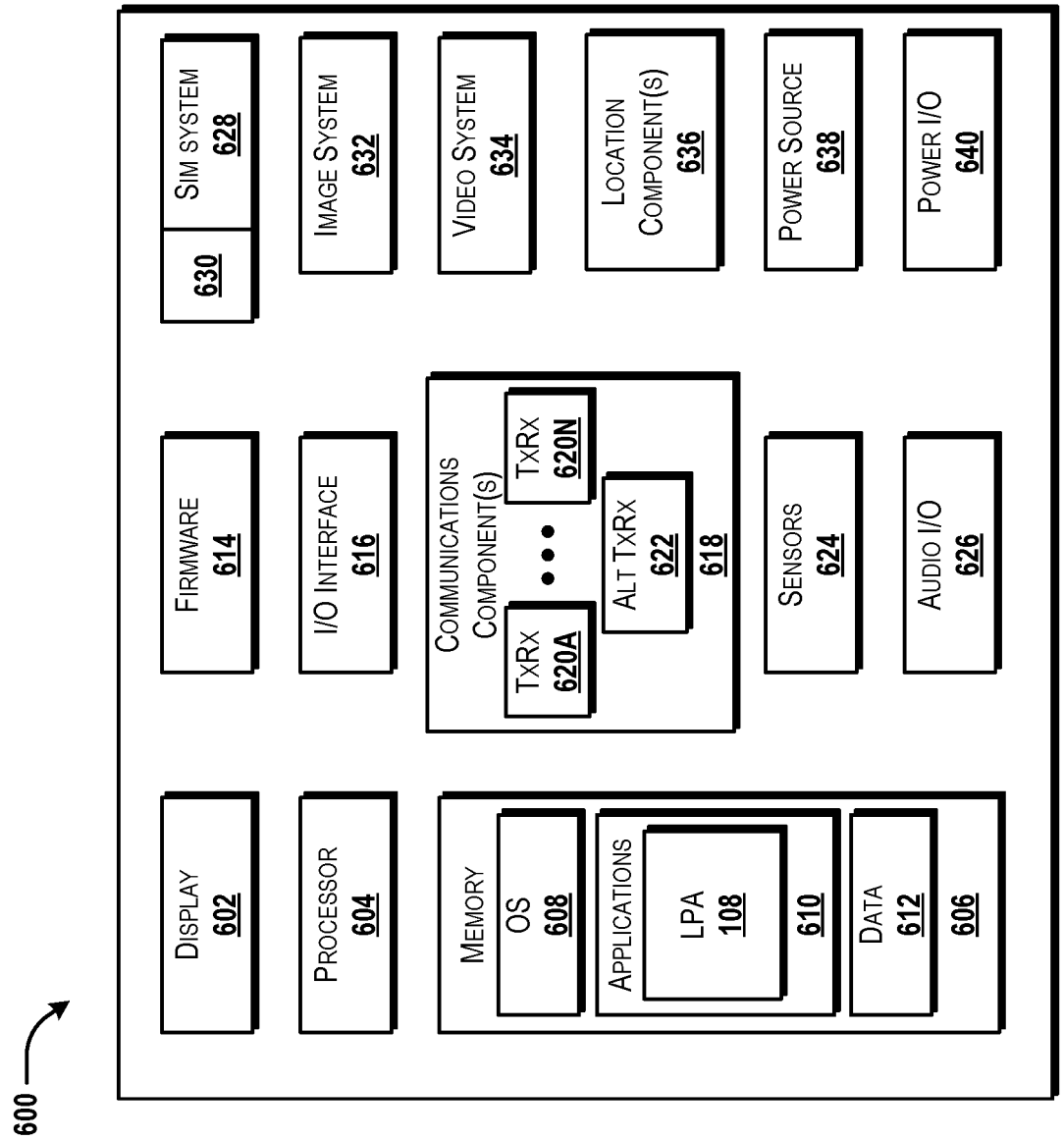
FIG. 6 is a block diagram illustrating an example mobile device configured to interact with a location and proximity service, according to some illustrative embodiments of the concepts and technologies described herein.

Turning now to FIG. 6, an illustrative mobile device 600 and components thereof will be described. In some embodiments, the user device 102 described above with reference to FIG. 1 can be configured as and/or can have an architecture similar or identical to the mobile device 600 described herein in FIG. 6. It should be understood, however, that the user device 102 may or may not include the functionality described herein with reference to FIG. 6. While connections are not shown between the various components illustrated in FIG. 6, it should be understood that some, none, or all of the components illustrated in FIG. 6 can be configured to interact with one another to carry out various device functions. In some embodiments, the components are arranged so as to communicate via one or more busses (not shown). Thus, it should be understood that FIG. 6 and the following description are intended to provide a general understanding of a suitable environment in which various aspects of embodiments can be implemented, and should not be construed as being limiting in any way.

As illustrated in FIG. 6, the mobile device 600 can include a display 602 for displaying data. According to various embodiments, the display 602 can be configured to display various graphical user interface ("GUI") elements such as, for example, opt-in screens, location screens, proximity screens, text, images, video, virtual keypads and/or keyboards, messaging data, notification messages, metadata, internet content, device status, time, date, calendar data, device preferences, map and location data, combinations thereof, and/or the like. The mobile device 600 also can include a processor 604 and a memory or other data storage device ("memory") 606. The processor 604 can be configured to process data and/or can execute computer-executable instructions stored in the memory 606. The computer-executable instructions executed by the processor 604 can include, for example, an operating system 608, one or more applications 610 such as the location and proximity application 108, other computer-executable instructions stored in a memory 606, or the like. In some embodiments, the applications 610 also can include a UI application (not illustrated in FIG. 6).

The UI application can interface with the operating system 608, such as the operating system 106 shown in FIG. 1, to facilitate user interaction with functionality and/or data stored at the mobile device 600 and/or stored elsewhere. In some embodiments, the operating system 608 can include a member of the SYMBIAN OS family of operating systems from SYMBIAN LIMITED, a member of the WINDOWS MOBILE OS and/or WINDOWS PHONE OS families of operating systems from MICROSOFT CORPORATION, a member of the PALM WEBOS family of operating systems from HEWLETT PACKARD CORPORATION, a member of the BLACKBERRY OS family of operating systems from RESEARCH IN MOTION LIMITED, a member of the IOS family of operating systems from APPLE INC., a member of the ANDROID OS family of operating systems from GOOGLE INC., and/or other operating systems. These operating systems are merely illustrative of some contemplated operating systems that may be used in accordance with various embodiments of the concepts and technologies described herein and therefore should not be construed as being limiting in any way.

The UI application can be executed by the processor 604 to aid a user in entering content, opting in, entering locations, entering proximity information, configuring settings, manipulating address book content and/or settings, multimode interaction, interacting with other applications 610, and otherwise facilitating user interaction with the operating system 608, the applications 610, and/or other types or instances of data 612 that can be stored at the mobile device 600. The data 612 can include, for example, the location and proximity application 108 and/or other applications or program modules. According to various embodiments, the data 612 can include, for example, presence applications, visual voice mail applications, messaging applications, text-to-speech and speech-to-text applications, add-ons, plug-ins, email applications, music applications, video applications, camera applications, location-based service applications, power conservation applications, game applications, productivity applications, entertainment applications, enterprise applications, combinations thereof, and the like. The applications 610, the data 612, and/or portions thereof can be stored in the memory 606 and/or in a firmware 614, and can be executed by the processor 604.

It can be appreciated that, at least by virtue of storage of the instructions corresponding to the applications 610 and/or other instructions embodying other functionality illustrated and described herein in the memory 606, and/or by virtue of the instructions corresponding to the applications 610 and/or other instructions embodying other functionality illustrated and described herein being accessed and/or executed by the processor 604, the mobile device 600 is a special-purpose mobile device that can facilitate providing the functionality illustrated and described herein. The firmware 614 also can store code for execution during device power up and power down operations. It can be appreciated that the firmware 614 can be stored in a volatile or non-volatile data storage device including, but not limited to, the memory 606 and/or a portion thereof.

The mobile device 600 also can include an input/output ("I/O") interface 616. The I/O interface 616 can be configured to support the input/output of data such as location information, sensor data 112, fingerprints 120 and/or components thereof (e.g., the sound fingerprints 122 and/or the scent fingerprints 124), user information, organization information, presence status information, user IDs, passwords, and application initiation (start-up) requests. In some embodiments, the I/O interface 616 can include a hardwire connection such as a universal serial bus ("USB") port, a mini-USB port, a micro-USB port, an audio jack, a PS2 port, an IEEE 1394 ("FIREWIRE") port, a serial port, a parallel port, an Ethernet (RJ45 or RJ48) port, a telephone (RJ11 or the like) port, a proprietary port, combinations thereof, or the like.

In some embodiments, the mobile device 600 can be configured to synchronize with another device to transfer content to and/or from the mobile device 600. In some embodiments, the mobile device 600 can be configured to receive updates to one or more of the applications 610 via the I/O interface 616, though this is not necessarily the case. In some embodiments, the I/O interface 616 accepts I/O devices such as keyboards, keypads, mice, interface tethers, printers, plotters, external storage, touch/multi-touch screens, touch pads, trackballs, joysticks, microphones, remote control devices, displays, projectors, medical equipment (e.g., stethoscopes, heart monitors, and other health metric monitors), modems, routers, external power sources, docking stations, combinations thereof, and the like. It should be appreciated that the I/O interface 616 may be used for communications between the mobile device 600 and a network device or local device.

The mobile device 600 also can include a communications component 618. The communications component 618 can be configured to interface with the processor 604 to facilitate wired and/or wireless communications with one or more networks such as the network 104 described herein. In some embodiments, other networks include networks that utilize non-cellular wireless technologies such as WI-FI or WIMAX. In some embodiments, the communications component 618 includes a multimode communications subsystem for facilitating communications via the cellular network and one or more other networks.

The communications component 618, in some embodiments, includes one or more transceivers. The one or more transceivers, if included, can be configured to communicate over the same and/or different wireless technology standards with respect to one another. For example, in some embodiments one or more of the transceivers of the communications component 618 may be configured to communicate using GSM, CDMAONE, CDMA2000, LTE, and various other 2G, 2.5G, 3G, 4G, 5G, and greater generation technology standards. Moreover, the communications component 618 may facilitate communications over various channel access methods (which may or may not be used by the aforementioned standards) including, but not limited to, TDMA, FDMA, W-CDMA, OFDM, SDMA, and the like.

In addition, the communications component 618 may facilitate data communications using GPRS, EDGE, the HSPA protocol family including HSDPA, EUL or otherwise termed HSUPA, HSPA+, and various other current and future wireless data access standards. In the illustrated embodiment, the communications component 618 can include a first transceiver ("TxRx") 620A that can operate in a first communications mode (e.g., GSM). The communications component 618 also can include an $N^{th}$ transceiver ("TxRx") 620N that can operate in a second communications mode relative to the first transceiver 620A (e.g., UMTS). While two transceivers 620A-N (hereinafter collectively and/or generically referred to as "transceivers 620") are shown in FIG. 6, it should be appreciated that less than two, two, and/or more than two transceivers 620 can be included in the communications component 618.

The communications component 618 also can include an alternative transceiver ("Alt TxRx") 622 for supporting other types and/or standards of communications. According to various contemplated embodiments, the alternative transceiver 622 can communicate using various communications technologies such as, for example, WI-FI, WIMAX, BLUETOOTH, infrared, infrared data association ("IRDA"), near field communications ("NFC"), other RF technologies, combinations thereof, and the like. In some embodiments, the communications component 618 also can facilitate reception from terrestrial radio networks, digital satellite radio networks, internet-based radio service networks, combinations thereof, and the like. The communications component 618 can process data from a network such as the Internet, an intranet, a broadband network, a WI-FI hotspot, an Internet service provider ("ISP"), a digital subscriber line ("DSL") provider, a broadband provider, combinations thereof, or the like.

The mobile device 600 also can include one or more sensors 624. The sensors 624 can include temperature sensors, light sensors, air quality sensors, movement sensors, orientation sensors, noise sensors, proximity sensors, or the like. As such, it should be understood that the sensors 624 can include, but are not limited to, accelerometers, magnetometers, gyroscopes, infrared sensors, noise sensors, microphones, combinations thereof, or the like. Additionally, audio capabilities for the mobile device 600 may be provided by an audio I/O component 626. The audio I/O component 626 of the mobile device 600 can include one or more speakers for the output of audio signals, one or more microphones for the collection and/or input of audio signals, and/or other audio input and/or output devices.

The illustrated mobile device 600 also can include a subscriber identity module ("SIM") system 628. The SIM system 628 can include a universal SIM ("USIM"), a universal integrated circuit card ("UICC") and/or other identity devices. The SIM system 628 can include and/or can be connected to or inserted into an interface such as a slot interface 630. In some embodiments, the slot interface 630 can be configured to accept insertion of other identity cards or modules for accessing various types of networks. Additionally, or alternatively, the slot interface 630 can be configured to accept multiple subscriber identity cards. Because other devices and/or modules for identifying users and/or the mobile device 600 are contemplated, it should be understood that these embodiments are illustrative, and should not be construed as being limiting in any way.

The mobile device 600 also can include an image capture and processing system 632 ("image system"). The image system 632 can be configured to capture or otherwise obtain photos, videos, and/or other visual information. As such, the image system 632 can include cameras, lenses, charge-coupled devices ("CCDs"), combinations thereof, or the like. The mobile device 600 may also include a video system 634. The video system 634 can be configured to capture, process, record, modify, and/or store video content. Photos and videos obtained using the image system 632 and the video system 634, respectively, may be added as message content to an MMS message, email message, and sent to another mobile device. The video and/or photo content also can be shared with other devices via various types of data transfers via wired and/or wireless communication devices as described herein.

The mobile device 600 also can include one or more location components 636. The location components 636 can be configured to send and/or receive signals to determine a geographic location of the mobile device 600. According to various embodiments, the location components 636 can send and/or receive signals from global positioning system ("GPS") devices, assisted-GPS ("A-GPS") devices, WI-FI/WIMAX and/or cellular network triangulation data, combinations thereof, and the like. The location component 636 also can be configured to communicate with the communications component 618 to retrieve triangulation data for determining a location of the mobile device 600. In some embodiments, the location component 636 can interface with cellular network nodes, telephone lines, satellites, location transmitters and/or beacons, wireless network transmitters and receivers, combinations thereof, and the like. In some embodiments, the location component 636 can include and/or can communicate with one or more of the sensors 624 such as, a compass, an accelerometer, and/or a gyroscope to determine the orientation of the mobile device 600. Using the location component 636, the mobile device 600 can generate and/or receive data to identify its geographic location, or to transmit data used by other devices to determine the location of the mobile device 600. The location component 636 may include multiple components for determining the location and/or orientation of the mobile device 600.

The illustrated mobile device 600 also can include a power source 638. The power source 638 can include one or more batteries, power supplies, power cells, and/or other power subsystems including alternating current ("AC") and/or direct current ("DC") power devices. The power source 638 also can interface with an external power system or charging equipment via a power I/O component 640. Because the mobile device 600 can include additional and/or alternative components, the above embodiment should be understood as being illustrative of one possible operating environment for various embodiments of the concepts and technologies described herein. The described embodiment of the mobile device 600 is illustrative, and should not be construed as being limiting in any way.

Figure 7:
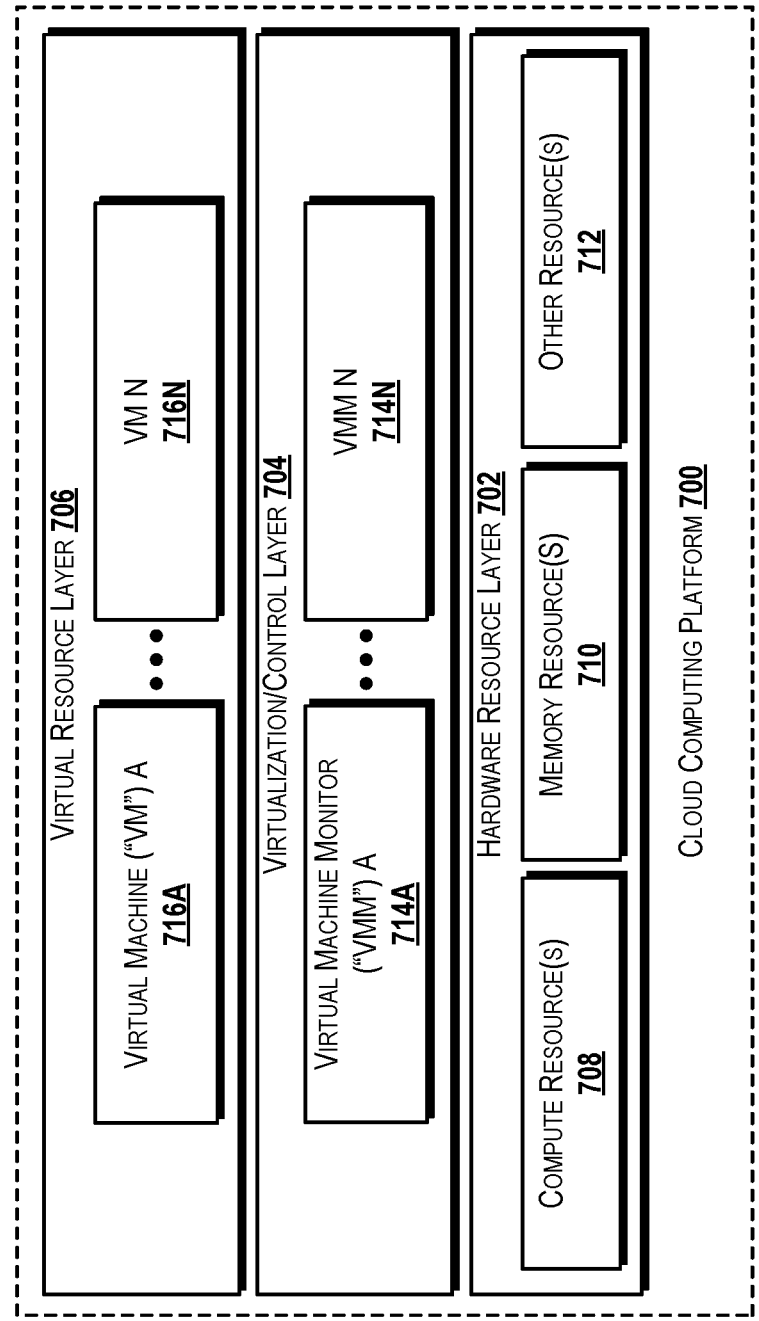
FIG. 7 is a diagram illustrating a computing environment capable of implementing aspects of the concepts and technologies disclosed herein, according to some illustrative embodiments of the concepts and technologies described herein.

FIG. 7 illustrates an illustrative architecture for a cloud computing platform 700 that can be capable of executing the software components described herein for using scent fingerprints and sound fingerprints for location and proximity determinations and/or for interacting with the location and proximity application 108, the location and proximity service 116, and/or other entities. Thus, it can be appreciated that in some embodiments of the concepts and technologies disclosed herein, the cloud computing platform 700 illustrated in FIG. 7 can be used to provide the functionality described herein with respect to the server computer 118.

The cloud computing platform 700 thus may be utilized to execute any aspects of the software components presented herein. Thus, according to various embodiments of the concepts and technologies disclosed herein, the location and proximity service 116 can be implemented, at least in part, on or by elements included in the cloud computing platform 700 illustrated and described herein. Those skilled in the art will appreciate that the illustrated cloud computing platform 700 is a simplification of but only one possible implementation of an illustrative cloud computing platform, and as such, the illustrated cloud computing platform 700 should not be construed as being limiting in any way.

In the illustrated embodiment, the cloud computing platform 700 can include a hardware resource layer 702, a virtualization/control layer 704, and a virtual resource layer 706. These layers and/or other layers can be configured to cooperate with each other and/or other elements of a cloud computing platform 700 to perform operations as will be described in detail herein. While connections are shown between some of the components illustrated in FIG. 7, it should be understood that some, none, or all of the components illustrated in FIG. 7 can be configured to interact with one another to carry out various functions described herein. In some embodiments, the components are arranged so as to communicate via one or more networks such as, for example, the network 104 illustrated and described hereinabove (not shown in FIG. 7). Thus, it should be understood that FIG. 7 and the following description are intended to provide a general understanding of a suitable environment in which various aspects of embodiments can be implemented, and should not be construed as being limiting in any way.

The hardware resource layer 702 can provide hardware resources. In the illustrated embodiment, the hardware resources can include one or more compute resources 708, one or more memory resources 710, and one or more other resources 712. The compute resource(s) 708 can include one or more hardware components that can perform computations to process data, and/or to execute computer-executable instructions of one or more application programs, operating systems, services, and/or other software including, but not limited to, the location and proximity service 116 illustrated and described herein.

According to various embodiments, the compute resources 708 can include one or more central processing units ("CPUs"). The CPUs can be configured with one or more processing cores. In some embodiments, the compute resources 708 can include one or more graphics processing units ("GPUs"). The GPUs can be configured to accelerate operations performed by one or more CPUs, and/or to perform computations to process data, and/or to execute computer-executable instructions of one or more application programs, operating systems, and/or other software that may or may not include instructions that are specifically graphics computations and/or related to graphics computations. In some embodiments, the compute resources 708 can include one or more discrete GPUs. In some other embodiments, the compute resources 708 can include one or more CPU and/or GPU components that can be configured in accordance with a co-processing CPU/GPU computing model. Thus, it can be appreciated that in some embodiments of the compute resources 708, a sequential part of an application can execute on a CPU and a computationally-intensive part of the application can be accelerated by the GPU. It should be understood that this example is illustrative, and therefore should not be construed as being limiting in any way.

In some embodiments, the compute resources 708 also can include one or more system on a chip ("SoC") components. It should be understood that the SoC component can operate in association with one or more other components as illustrated and described herein, for example, one or more of the memory resources 710 and/or one or more of the other resources 712. In some embodiments in which an SoC component is included, the compute resources 708 can be or can include one or more embodiments of the SNAPDRAGON brand family of SoCs, available from QUALCOMM of San Diego, California; one or more embodiment of the TEGRA brand family of SoCs, available from NVIDIA of Santa Clara, California; one or more embodiment of the HUMMINGBIRD brand family of SoCs, available from SAMSUNG of Seoul, South Korea; one or more embodiment of the Open Multimedia Application Platform ("OMAP") family of SoCs, available from TEXAS INSTRUMENTS of Dallas, Texas; one or more customized versions of any of the above SoCs; and/or one or more other brand and/or one or more proprietary SoCs.

The compute resources 708 can be or can include one or more hardware components arranged in accordance with an ARM architecture, available for license from ARM HOLDINGS of Cambridge, United Kingdom. Alternatively, the compute resources 708 can be or can include one or more hardware components arranged in accordance with an x86 architecture, such as an architecture available from INTEL CORPORATION of Mountain View, California, and others. Those skilled in the art will appreciate the implementation of the compute resources 708 can utilize various computation architectures and/or processing architectures. As such, the various example embodiments of the compute resources 708 as mentioned hereinabove should not be construed as being limiting in any way. Rather, implementations of embodiments of the concepts and technologies disclosed herein can be implemented using compute resources 708 having any of the particular computation architecture and/or combination of computation architectures mentioned herein as well as other architectures.

Although not separately illustrated in FIG. 7, it should be understood that the compute resources 708 illustrated and described herein can host and/or execute various services, applications, portals, and/or other functionality illustrated and described herein. Thus, the compute resources 708 can host and/or can execute the location and proximity service 116 or other applications or services illustrated and described herein (e.g., functionality associated with the location and proximity application 108, etc.).

The memory resource(s) 710 can include one or more hardware components that can perform or provide storage operations, including temporary and/or permanent storage operations. In some embodiments, the memory resource(s) 710 can include volatile and/or non-volatile memory implemented in any method or technology for storage of information such as computer-readable instructions, data structures, program modules, or other data disclosed herein. Computer storage media is defined hereinabove and therefore should be understood as including, in various embodiments, random access memory ("RAM"), read-only memory ("ROM"), Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium that can be used to store data and that can be accessed by the compute resources 708, subject to the definition of "computer storage media" provided above (e.g., as excluding waves and signals per se and/or communication media as defined in this application).

Although not illustrated in FIG. 7, it should be understood that the memory resources 710 can host or store the various data illustrated and described herein including, but not limited to, sensor data 112, the fingerprints 120, the sound fingerprints 122, the scent fingerprints 124, and/or other data, if desired. It should be understood that this example is illustrative, and therefore should not be construed as being limiting in any way.

The other resource(s) 712 can include any other hardware resources that can be utilized by the compute resources(s) 708 and/or the memory resource(s) 710 to perform operations. The other resource(s) 712 can include one or more input and/or output processors (e.g., a network interface controller and/or a wireless radio), one or more modems, one or more codec chipsets, one or more pipeline processors, one or more fast Fourier transform ("FFT") processors, one or more digital signal processors ("DSPs"), one or more speech synthesizers, combinations thereof, or the like.

The hardware resources operating within the hardware resource layer 702 can be virtualized by one or more virtual machine monitors ("VMMs") 714A-714N (also known as "hypervisors;" hereinafter "VMMs 714"). The VMMs 714 can operate within the virtualization/control layer 704 to manage one or more virtual resources that can reside in the virtual resource layer 706. The VMMs 714 can be or can include software, firmware, and/or hardware that alone or in combination with other software, firmware, and/or hardware, can manage one or more virtual resources operating within the virtual resource layer 706.

The virtual resources operating within the virtual resource layer 706 can include abstractions of at least a portion of the compute resources 708, the memory resources 710, the other resources 712, or any combination thereof. These abstractions are referred to herein as virtual machines ("VMs"). In the illustrated embodiment, the virtual resource layer 706 includes VMs 716A-716N (hereinafter "VMs 716").

Based on the foregoing, it should be appreciated that systems and methods for using scent fingerprints and sound fingerprints for location and proximity determinations have been disclosed herein. Although the subject matter presented herein has been described in language specific to computer structural features, methodological and transformative acts, specific computing machinery, and computer-readable media, it is to be understood that the concepts and technologies disclosed herein are not necessarily limited to the specific features, acts, or media described herein. Rather, the specific features, acts and mediums are disclosed as example forms of implementing the concepts and technologies disclosed herein.

The subject matter described above is provided by way of illustration only and should not be construed as limiting. Various modifications and changes may be made to the subject matter described herein without following the example embodiments and applications illustrated and described, and without departing from the true spirit and scope of the embodiments of the concepts and technologies disclosed herein.

The invention claimed is:

1. A system comprising:
   a processor; and
   a memory that stores computer-executable instructions that, when executed by the processor, cause the processor to perform operations comprising:
      detecting, using a movement sensor and orientation sensor of a user device, movements of the user device within an environment comprising an indoor location at which global positioning system location is unavailable;
      determining if a fingerprint associated with the user device and the environment is available, wherein the fingerprint comprises a sound fingerprint, a scent fingerprint, and usage data defining resource usage of the user device at locations within the environment, the resource usage comprising the user device accessing a resource that is hosted by a computing device that is not located at the environment;

obtaining the fingerprint associated with the user device and the environment;

obtaining an instance of sensor data comprising a current scent detected at the environment by a scent sensor of the user device, and a current sound detected at the environment by the user device, wherein the current scent comprises a current chemical makeup associated with the current scent and a current intensity of the current scent expressed in parts per million;

determining, based on the instance of sensor data and the fingerprint associated with the user device and the environment, a location and proximity of the user device within the environment;

determining, based on the location and proximity of the user device, that an action should be taken; and in response to determining that the action should be taken, triggering the action, wherein the action comprises generating a first command and sending the first command to the computing device, wherein the computing device is configured to instantiate the resource and make the resource available to the user device in response to receiving the first command, and generating a second command and sending the second command to the user device, wherein the user device is configured to activate an application to access the resource in response to receiving the second command.

2. The system of claim 1, wherein obtaining the fingerprint comprises:

obtaining a further instance of sensor data;

determining, based on the further instance of sensor data, a location of the user device in the environment, the scent fingerprint at the location of the user device in the environment, the sound fingerprint at the location of the user device in the environment, and the resource usage of the user device at the location of the user device in the environment;

recording the fingerprint, wherein the fingerprint comprises an identifier of the user device, location data that identifies the location of the user device in the environment, the sound fingerprint at the location of the user device in the environment, the scent fingerprint at the location of the user device in the environment, and the resource usage of the user device at the location of the user device in the environment; and storing the fingerprint.

3. The system of claim 1, wherein the sound fingerprint comprises:

a first sound recorded at the location of the user device in the environment, a first level associated with the first sound, and a first frequency of the first sound; and a second sound recorded at the location of the user device in the environment, a second level associated with the second sound, and a second frequency of the second sound.

4. The system of claim 1, wherein the scent fingerprint comprises:

a first chemical makeup associated with a first scent detected by the scent sensor of the user device at the location of the user device in the environment, and a first intensity of the first scent expressed in parts per million; and a second chemical makeup associated with a second scent detected by the scent sensor of the user device at the location of the user device in the environment, and a second intensity of the second scent expressed in parts per million.

5. The system of claim 1, wherein the computer-executable instructions, when executed by the processor, cause the processor to perform operations further comprising:

updating the fingerprint with additional information that reflects the access of the resource by the user device, resources that should be installed and made available based on the movements of the user device, and applications at the user device that should be activated based on the movements of the user device.

6. A method comprising:

detecting, at a computer comprising a processor and using a movement sensor and orientation sensor of a user device, movements of the user device within an environment comprising an indoor location at which global positioning system location is unavailable;

determining, by the processor, if a fingerprint associated with the user device and the environment is available, wherein the fingerprint comprises a sound fingerprint, a scent fingerprint, and usage data defining resource usage of the user device at locations within the environment, the resource usage comprising the user device accessing a resource that is hosted by a computing device that is not located at the environment;

obtaining, by the processor, the fingerprint associated with the user device and the environment;

obtaining, by the processor, an instance of sensor data comprising a current scent detected at the environment by a scent sensor of the user device, and a current sound detected at the environment by the user device, wherein the current scent comprises a current chemical makeup associated with the current scent and a current intensity of the current scent expressed in parts per million;

determining, by the processor and based on the instance of sensor data and the fingerprint associated with the user device and the environment, a location and proximity of the user device within the environment;

determining, based on the location and proximity of the user device, that an action should be taken; and in response to determining that the action should be taken, triggering the action, wherein the action comprises generating a first command and sending the first command to the computing device, wherein the computing device is configured to instantiate the resource and make the resource available to the user device in response to receiving the first command, and generating a second command and sending the second command to the user device, wherein the user device is configured to activate an application to access the resource in response to receiving the second command.

7. The method of claim 6, further comprising:

updating the fingerprint to reflect the access of the resource by the user device.

8. The method of claim 6, further comprising:
updating the fingerprint with additional information that depicts resources that should be installed and made available based on the movements of the user device.

9. The method of claim 6, further comprising:
updating the fingerprint with additional information that depicts applications at the user device that should be activated based on the movements of the user device.

10. The method of claim 6, further comprising:
determining, by the processor and based on a query sent to the user device and a response to the query received from the user device, if the user device has opted-in to use scent and sound to determine location and proximity.

11. The method of claim 6, wherein obtaining the fingerprint associated with the user device and the environment comprises creating the fingerprint.

12. The method of claim 6, wherein obtaining the fingerprint associated with the user device and the environment comprises retrieving the fingerprint.

13. The method of claim 6, wherein creating the fingerprint comprises:
obtaining a further instance of sensor data;
determining, based on the further instance of sensor data, a location of the user device in the environment, the scent fingerprint at the location of the user device in the environment, the sound fingerprint at the location of the user device in the environment, and the resource usage of the user device at the location of the user device in the environment;
recording the fingerprint, wherein the fingerprint comprises an identifier of the user device, location data that identifies the location of the user device in the environment, the sound fingerprint at the location of the user device in the environment, the scent fingerprint at the location of the user device in the environment, and the resource usage of the user device at the location of the user device in the environment; and
storing the fingerprint.

14. The method of claim 6, wherein the sound fingerprint comprises:
a first sound recorded at the location of the user device in the environment, a first level associated with the first sound, and a first frequency of the first sound; and
a second sound recorded at the location of the user device in the environment, a second level associated with the second sound, and a second frequency of the second sound.

15. The method of claim 6, wherein the scent fingerprint comprises:
a first chemical makeup associated with a first scent detected by the scent sensor of the user device at the location of the user device in the environment, and a first intensity of the first scent expressed in parts per million; and
a second chemical makeup associated with a second scent detected by the scent sensor of the user device at the location of the user device in the environment, and a second intensity of the second scent expressed in parts per million.

16. A computer storage medium having computer-executable instructions stored thereon that, when executed by a processor, cause the processor to perform operations comprising:
detecting, using a movement sensor and orientation sensor of a user device, movements of the user device within an environment comprising an indoor location at which global positioning system location is unavailable;
determining if a fingerprint associated with the user device and the environment is available, wherein the fingerprint comprises a sound fingerprint, a scent fingerprint, and usage data defining resource usage of the user device at locations within the environment, the resource usage comprising the user device accessing a resource that is hosted by a computing device that is not located at the environment;
obtaining the fingerprint associated with the user device and the environment;
obtaining an instance of sensor data comprising a current scent detected at the environment by a scent sensor of the user device, and a current sound detected at the environment by the user device, wherein the current scent comprises a current chemical makeup associated with the current scent and a current intensity of the current scent expressed in parts per million;
determining, based on the instance of sensor data and the fingerprint associated with the user device and the environment, a location and proximity of the user device within the environment;
determining, based on the location and proximity of the user device, that an action should be taken; and
in response to determining that the action should be taken, triggering the action, wherein the action comprises
generating a first command and sending the first command to the computing device, wherein the computing device is configured to instantiate the resource and make the resource available to the user device in response to receiving the first command, and
generating a second command and sending the second command to the user device, wherein the user device is configured to activate an application to access the resource in response to receiving the second command.

17. The computer storage medium of claim 16, wherein obtaining the fingerprint comprises:
obtaining a further instance of sensor data;
determining, based on the further instance of sensor data, a location of the user device in the environment, the scent fingerprint at the location of the user device in the environment, the sound fingerprint at the location of the user device in the environment, and the resource usage of the user device at the location of the user device in the environment;
recording the fingerprint, wherein the fingerprint comprises an identifier of the user device, location data that identifies the location of the user device in the environment, the sound fingerprint at the location of the user device in the environment, the scent fingerprint at the location of the user device in the environment, and the resource usage of the user device at the location of the user device in the environment; and
storing the fingerprint.

18. The computer storage medium of claim 16, wherein the sound fingerprint comprises:
a first sound recorded at the location of the user device in the environment, a first level associated with the first sound, and a first frequency of the first sound; and
a second sound recorded at the location of the user device in the environment, a second level associated with the second sound, and a second frequency of the second sound.

19. The computer storage medium of claim 16, wherein the scent fingerprint comprises:
- a first chemical makeup associated with a first scent detected by the scent sensor of the user device at the location of the user device in the environment, and a first intensity of the first scent expressed in parts per million; and
- a second chemical makeup associated with a second scent detected by the scent sensor of the user device at the location of the user device in the environment, and a second intensity of the second scent expressed in parts per million.

20. The computer storage medium of claim 16, wherein the computer-executable instructions, when executed by the processor, cause the processor to perform operations further comprising:
- updating the fingerprint with additional information that reflects the access of the resource by the user device, resources that should be installed and made available based on the movements of the user device, and applications at the user device that should be activated based on the movements of the user device.

* * * * *